(12) United States Patent
Buj Bello et al.

(10) Patent No.: US 9,981,049 B2
(45) Date of Patent: May 29, 2018

(54) SELECTIVE GENE THERAPY EXPRESSION SYSTEM

(71) Applicants: GENETHON, Evry (FR); CENTRE NATIONAL DE LA RECHERCHE SCIENTIFIQUE, Paris (FR)

(72) Inventors: Ana Maria Buj Bello, Paris (FR); Isabelle Richard, Corbeil Essonnes (FR)

(73) Assignees: GENETHON, Evry (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days. days.

(21) Appl. No.: 14/782,396

(22) PCT Filed: Apr. 10, 2014

(86) PCT No.: PCT/FR2014/050866
§ 371 (c)(1),
(2) Date: Oct. 5, 2015

(87) PCT Pub. No.: WO2014/167253
PCT Pub. Date: Oct. 16, 2014

(65) Prior Publication Data
US 2016/0058890 A1    Mar. 3, 2016

(30) Foreign Application Priority Data

Apr. 11, 2013 (FR) ...................... 13 53306

(51) Int. Cl.
| | |
|---|---|
| *A61K 48/00* | (2006.01) |
| *C12N 9/16* | (2006.01) |
| *C12N 9/64* | (2006.01) |
| *A61K 38/46* | (2006.01) |
| *A61K 38/48* | (2006.01) |
| *C12N 15/86* | (2006.01) |
| *C07K 14/47* | (2006.01) |

(52) U.S. Cl.
CPC ........ *A61K 48/0066* (2013.01); *A61K 38/465* (2013.01); *A61K 38/4873* (2013.01); *A61K 48/0058* (2013.01); *A61K 48/0075* (2013.01); *C12N 9/16* (2013.01); *C12N 9/6472* (2013.01); *C12N 15/86* (2013.01); *C07K 14/4707* (2013.01); *C12N 2750/14132* (2013.01); *C12N 2750/14143* (2013.01); *C12N 2830/008* (2013.01); *C12Y 301/03048* (2013.01); *C12Y 304/22054* (2013.01)

(58) Field of Classification Search
CPC ................................................. A61K 48/0066
See application file for complete search history.

(56) References Cited

FOREIGN PATENT DOCUMENTS

| | | | |
|---|---|---|---|
| WO | WO9616175 | * | 5/1996 |
| WO | 2010/148010 A1 | | 12/2010 |

OTHER PUBLICATIONS

Lagos-Quintana et al (RNA 9 (2), 175-179 (2003).*
Al-Qusairi et al., "T-tubule disorganization and defective excitation-contraction coupling in muscle fibers lacking myotubularin lipid phosphatase," *PNAS* 106(44):18763-18768 (Nov. 3, 2009).
Bartoli et al., "Safety and Efficacy of AAV-Medicated Calpain 3 Gene Transfer in a Mouse Model of Limb-Girdle Muscular Dystrophy Type 2A," *Molecular Therapy* 13(2):250-259 (Feb. 2006).
Beggs et al., "MTM1 mutation associated with x-linked myotubular myopathy in Labrador Retrievers," *PNAS* 107(33):14697-14702 (Aug. 17, 2010).
Bevilacqua et al., "'Necklace' fibers, a new histological marker of late-onset MTM1-related centronuclear myopathy," *Acta Neruopathol.* 117(3):283-291 Abstract (one page) (Mar. 2009).
Buj-Bello et al., "The lipid phosphatase myotubularin is essential for skeletal muscle maintenance but not for myogenesis in mice," *PNAS* 99(23):15060-15065 (Nov. 12, 2002).
Buj-Bello et al., "AAV-mediated intramuscular delivery of myotubularin corrects the myotubular myopathy phenotype in targeted murine muscle and suggests a function in plasma membrane homeostasis," *Human Molecular Genetics* 17(14):2132-2143 (2008).
Dowling et al., "Loss of Myotubularin Function Results in T-Tubule Disorganization in Zebrafish and Human Myotubular Myopathy,"*PLoS Genetics* 5(2):e1000372 (13 pages) (Feb. 2009).
Dowling et al., "Myotubular myopathy and the neuromuscular junction: a novel therapeutic approach from mouse models," *Disease Models & Mechanisms* 5:852-859 (2012).
Herman et al., "Medical complications in long-term survivors with X-linked myotubular myopathy," *J Pediatr.* 134(2):206-214 Abstract (one page) (Feb. 1999).
Hnia et al., "Myotubularin controls desmin dynamics in human and mouse skeletal intermediate filament architecture and mitochondrial muscle," *The Journal of Clinical Investigation* 121(1):70-85 (Jan. 2011).
Jungbluth et al., "Centronuclear (myotubular) myopathy," *Orphanet Journal of Rare Diseases* 3:26 (13 pages) (Sep. 25, 2008).
Karine et al., "Toxicity of uncontrolled activity of calpain 3," *Myology, 4th International Congress of Myology* p. 119 (2011).
Kelly et al., "MicroRNAs and the Regulation of Vector Tropism," *Molecular Therapy* 17(3):409-416 (Mar. 2009).
Laporte et al., "A gene mutated in X-linked myotubular myopathy defines a new putative tyrosine phosphatase family conserved in yeast," *Nat Genet.* 13(2):175-182 Abstract (one page) (Jun. 1996).
Lawlor et al., "Myotubularin-Deficient Myoblasts Display Increased Apoptosis, Delayed Proliferation, and Poor Cell Engraftment," *The American Journal of Pathology* 181(3):961-968 (Sep. 2012).

(Continued)

*Primary Examiner* — Anoop K Singh
*Assistant Examiner* — Magdalene K Sgagias
(74) *Attorney, Agent, or Firm* — Seed IP Law Group LLP

(57) ABSTRACT

The present invention relates to an expression system for systemic administration comprising a sequence encoding a protein, said expression system allowing:
    the expression at a therapeutically acceptable level of the protein in the target tissues including skeletal muscles and/or the peripheral nervous tissue; and
    the expression at toxically acceptable level of the protein in tissues other than the target tissues, especially in the heart.

10 Claims, 5 Drawing Sheets

(56) References Cited

OTHER PUBLICATIONS

Figure 1:
Figure 1:
Figure 1:
Figure 1:

Mendell et al., "Sustained Alpha-Sarcoglycan Gene Expression after Gene Transfer in Limb-Girdle Muscular Dystrophy, Type 2D," *Ann Neurol* 68:629-638 (2010).

Pierson et al., "Modeling the human MTM1 p.R69C mutation in murine Mtm1 results in exon 4 skipping and a less severe myotubular myopathy phenotype," *Human Molecular Genetics* 21(4):811-825 (2012).

Qiao et al., "Liver-specific microRNA-122 target sequences incorporated in AAV vectors efficiently inhibits transgene expression in the liver," *Gene Therapy* 18:403-410 (2011).

Walgren-Pettersson et al., "The linked recessive, autosomal dominant, myotubular myopathies: differential diagnosis of the X and autosomal recessive forms and present state of DNA studies," *J Med Genet* 32:673-679 (1995).

Wang et al., "Construction and analysis of compact muscle-specific promoters for AAV vectors," *Gene Therapy* 15:1489-1499 (2008).

Wang, "Gene Therapy and Muscles: The Use of Adeno-associated Virus—Where are We Today?" *Oper Tech Orthop* 20:136-143 (2010).

Xie et al., "MicroRNA-regulated, Systemetically Delivered rAAV9: A Step Closer to CNS-restricted Transgene Expression," www.moleculartherapy.org 19(3):526-535 (Mar. 2011).

Beggs et al., "Development of AAV-gene and protein-based therapies for X-linked myotubular myopathy," *Abstracts / Neuromuscular Disorders* 22:804-908 (one page) (2012).

Inagaki et al., "Robust Systemic Transduction with AAV9 Vectors in Mice: Efficient Global Cardiac Gene Transfer Superior to That of AAV8," *Mol Ther.* 14(1):45-53 (Jul. 2006).

\* cited by examiner

SELECTIVE GENE THERAPY EXPRESSION SYSTEM

STATEMENT REGARDING SEQUENCE LISTING

The Sequence Listing associated with this application is provided in text format in lieu of a paper copy, and is hereby incorporated by reference into the specification. The name of the text file containing the Sequence Listing is 390106_402USPC_SEQUENCE_LISTING.txt. The text file is 46.6 KB, was created on Oct. 1, 2015, and is being submitted electronically via EFS-Web.

TECHNICAL DOMAIN

This invention relates to gene therapy, in particular the treatment of diseases affecting skeletal muscles such as myotubular myopathy, caused by mutations in the MTM1 gene.

In this context, it proposes an expression system comprising a protein-encoding transgene that will ensure the production of a therapeutically effective amount of the protein in the target tissues, preferably the skeletal muscles, and a toxically acceptable amount of the protein in the non-target tissues, especially the heart.

PRIOR ART

X-linked myotubular myopathy (or XLMTM, OMIN 310400) is the most severe and common form of a group of diseases called centronuclear myopathy. The patients have already been affected during their foetal life, they show reduced mobility during gestation and have myopathy at birth which appears as non-progressive [1,2,3]. They have generalised muscle weakness and hypotonia, leading to respiratory failure and many die during the initial years of life despite intensive medical care. More atypically, less severe forms of myotubular myopathy also exist in male and female subjects with mild symptoms during childhood, which are aggravated during the first or second decades of their life [4].

The skeletal muscles of the affected subjects contain small fibres with an altered distribution of organelles, such as nuclei and mitochondria, which are typically located in the centre of the fibres or, in less severe cases, are arranged in the form of a collar in the subsarcolemmal region [4,5].

The disease results from inactivating mutations in the ubiquitously expressed MTM1 gene, which encodes a phosphoinositide phosphatase called myotubularin [6].

Animal models of the disease are currently seen in zebrafish, mice and dogs [7,8,9,10]. Studies conducted in these models have shown that in the skeletal muscle, myotubularin plays a role in a variety of mechanisms, including the organisation of the T-tubule and the intermediate filament, the excitation-contraction coupling, the transmission of the neuromuscular junction, and the survival and proliferation of satellite cells [11,12,13,14].

The gene replacement therapy by means of a vector represents a potential therapeutic approach for myotubular myopathy. Thus, it was indicated as proof of concept that a single intramuscular injection of a recombinant adeno-associated viral vector (AAV) in mice having a muscle-specific symptomatic impairment of myotubularin (mKO) was capable of improving the pathology and function of the targeted muscles [15].

The question of treatment of muscular disorders remains crucial. Gene transfer, in particular by means of vectors derived from adeno-associated viruses which are found to be tools particularly suitable for muscle transfection, is a particularly promising approach. It involves administration of an intact copy of the gene to the patient, for the production of a functional protein compensating the mutated and inactive protein produced by said subject.

In the case of muscle diseases, the administration may be performed by local injection in the muscles of the vector carrying the transgene. However, systemic administration is preferred clinically, which means that the transgene can be found in the various tissues of the body.

Typically, the transgene is placed under the control of regulatory sequences governing its expression, in particular with regard to the level of expression or the tissue specificity of the expression. Thus and in the case of gene therapy of a muscle disease, a promoter governing an expression more specifically in the muscle may be preferred. For example, a synthetic promoter C5-12 has been developed, which is well known to the person skilled in the art and supposed to promote gene expression in muscles.

However, there is a clear need to develop new tools for gene therapy for treating neuromuscular diseases, leading to the production of effective amounts of protein in the target tissue to compensate for the lack of activity of the mutated proteins, and which are otherwise safe for the treated patients.

DESCRIPTION OF THE INVENTION

This invention is based on the identification by the inventors, that after systemic administration, an expression system intended for the production of a protein in a target tissue, preferably skeletal muscles, can simultaneously lead to an expression in other tissues and organs potentially toxic, rendering said system unsuitable for therapeutic use.

This invention provides technical solutions for this newly identified problem, particularly regarding cardiac leakages related to the skeletal muscle-specific expression of a transgene.

More broadly, this involves the following for a given expression system:
  determining if the system exhibits toxicity;
  determining the tissue(s) in which it exhibits toxicity;
  providing means to reduce this toxicity to an acceptable level.

Proteins referred to in this invention are thus those that exhibit toxicity in at least one tissue, particularly in a non-target tissue, when expressed from a given expression system.

Advantageously, the expression system is administered systemically in the body, particularly in an animal, and more preferably in humans.

Preferably, the analysis of toxicity is performed in a body with a defective copy of the sequence encoding the protein, i.e. in a body with the condition being treated, for example, a "Knockout" (KO) animal model. Indeed, if in the context of the invention, cardiac toxicity was observed for expression systems encoding myotubularin or calpain 3, it was detected only in KO mice in the case of myotubularin. In other words, a toxicity analysis that, according to usual practice, would have been performed in a healthy animal, would not have revealed this toxicity.

Thus and in general, this invention relates to an expression system comprising a sequence encoding a protein, the said expression system allowing:

the expression at a therapeutically acceptable level of the protein in the target tissue(s); and the expression at a toxically acceptable level of the protein in tissues other than the target tissue, i.e. in non-target tissues.

According to the invention, the target tissue is preferably defined as the tissue or organ in which the protein is to play a therapeutic role, especially in cases where the native gene encoding this protein is defective. According to a particular embodiment of the invention, the target tissue designates the striated skeletal muscles, hereafter referred to as skeletal muscles, i.e. all the muscles involved in motor ability including the diaphragm. These muscles are particularly affected in diseases called myopathy. Another potential target tissue is the peripheral nervous tissue, which can also be affected in neuromuscular diseases. Advantageously, the target tissue thus includes skeletal muscles and/or the peripheral nervous tissue.

According to the invention, the non-target tissues are preferably defined as tissues or organs in which the protein has no therapeutic role to play, and optionally, in which the presence of the protein exceeding the endogenous quantity may prove to be harmful or even fatal, and therefore toxic.

In the context of the invention, tissues that are to be protected from this potential toxicity are preferably:
the heart or cardiac striated muscle;
the liver;
the brain;
the lungs;
the kidney; and/or
the smooth muscles, in particular the gastrointestinal tract.

These are vital organs or tissues in which the gene expression systems tend to accumulate.

In the context of the invention, the heart muscle appears to be a tissue of particular interest as demonstrated at least for myotubularin and calpain 3. According to a particular embodiment, the expression system allows an expression at a toxically acceptable level of the protein in the heart.

Thus, and according to a particular aspect, the present invention relates to an expression system comprising a sequence encoding a protein, said expression system allowing:
the expression at a therapeutically acceptable level of the protein in the target tissues including skeletal muscles and/or the peripheral nervous tissue; and
the expression at toxically acceptable level of the protein in tissues other than the target tissues, especially in the heart.

According to a first characteristic, the expression system of the invention comprises a sequence encoding a protein, corresponding to a transgene. In the context of the invention, the term "transgene" refers to a sequence, preferably an open reading frame, provided in trans using the expression system of the invention.

According to a particular embodiment, this sequence is a copy, identical or equivalent, of an endogenous sequence present in the genome of the body into which the expression system is introduced. According to another particular embodiment, the endogenous sequence has one or more mutations rendering the protein partially or fully non-functional or even absent (lack of expression or activity of the endogenous protein), particularly in target tissues, i.e. skeletal muscles. In other words and preferably, the expression system of the invention is intended to be administered to a subject having a defective copy of the sequence encoding the protein and having an associated pathology. In this context, the protein encoded by the sequence carried by the expression system of the invention can therefore be defined as a protein whose mutation causes a neuromuscular disorder.

According to another embodiment, this involves a sequence that encodes a protein capable of "compensating" for the failure of a defective protein (regarding its expression or activity) in the subject to whom the expression system of the invention is administered. Thus and by way of example in relation to neuromuscular pathologies:

utrophin may be used in place of a mutated and deficient dystrophin;

decorin, fibromodulin and lumican help to compensate for the muscle wasting observed in the case of neuromuscular diseases;

activin also helps increase muscle mass in diseases whose cause is not a mutation of this protein.

Thus and more generally, the sequence carried by the expression system of the invention can be defined as encoding a protein having a therapeutic activity in the context of a neuromuscular disease. The concept of therapeutic activity is defined as below in connection with the term "therapeutically acceptable level".

The sequence encoding the protein is a nucleic acid sequence and may in particular be a DNA (deoxyribonucleic acid), an RNA (ribonucleic acid) or a cDNA (complementary deoxyribonucleic acid).

Advantageously, said sequence encodes a functional protein, i.e. a protein capable of ensuring its native or essential function, especially in the skeletal muscle. For each protein of interest, the desired activity and the sequence necessary for obtaining this activity can be defined.

According to a preferred embodiment, said sequence encodes the native protein, said protein being preferably of human origin. It may also be a derivative or a fragment of this protein, provided that the derivative or fragment retains the desired activity. Preferably, the term "derivative" or "fragment" refers to a protein sequence having at least 60%, preferably 70%, even more preferably 80% or even 90%, 95% or 99% identity with the human sequence of the protein of interest. Proteins with other origins (non-human mammals, etc.) or truncated, or even mutated, but active proteins are for instance designated. Thus and in the context of the invention, the term "protein" is understood as the full-length protein regardless of its origin, as well as functional derivatives and fragments thereof.

In the context of the invention, the proteins allowing the therapeutic treatment of neuromuscular diseases that may affect skeletal muscles and/or the peripheral nervous tissue are encompassed. The proteins enabling the therapeutic treatment of diseases affecting the skeletal muscles, generically called "myopathy", are more particularly referred to.

In a particular aspect, these diseases are caused by mutations in at least one gene causing non-production of the protein or production of a fully or partially non-functional protein. According to the invention, the expression system helps produce this protein in an active form and in a quantity that at least partially compensates for the absence of the native protein, or another protein capable of compensating for the absence of the native protein. The administration of the expression system thus makes it possible to improve or restore a normal phenotype in the target tissue(s), particularly the skeletal muscles, in terms of mobility and breathing.

A protein having a benefit particularly in the context of the present invention is myotubularin of human origin (SEQ ID NO: 1), murine (SEQ ID NO: 2) or canine (SEQ ID NO: 3). Any sequence encoding these proteins, functional therapeutical derivatives or fragments thereof, can be implemented as part of the expression system of the invention. Thus, by way of example, the corresponding nucleotide sequences (cDNA) are the sequences SEQ ID NO: 4, 5 (or 14) and 6, respectively.

Mutations in the MTM1 gene result, in a known manner, in a muscle disease called myotubular myopathy (MTM or XLMTM). Thus and according to the strategy for replacement or transfer of the gene, the provision in trans of a sequence encoding a therapeutic myotubularin, which is for example native, helps treat this pathology.

In another embodiment, the protein of interest is calpain 3 (CAPN3) whose mutations cause in particular a recessive autosomal genetic disease called type 2A limb-girdle dystrophy (LGMD 2A or calpainopathy, OMIN 253600). For example, human calpain 3 has the sequence SEQ ID NO: 7. Thus and as described above, any sequence that encodes a therapeutic calpain 3, for example that of sequence SEQ ID NO: 7, or a derivative or fragment thereof, may be present in an expression system of the invention. It may, for example, be the cDNA sequence shown in SEQ ID NO: 8, or the nucleotides 307 to 2772 corresponding to the open reading frame thereof.

Given below is a non-exhaustive list of proteins involved in diseases affecting the skeletal muscles and referred to in this invention: Sarcoglycan (α, β, γ, δ), Dystrophin, Dysferlin (DYSF), Selenoprotein 1 (SEPN1), Amphyphisine 2 (BIN1), dynamien 2 (DNM2), cofilin 2 (CFL2), troponin T (TNNT1), tropomyosin 3 (TPM3), ACTA1, contactin 1 (CNTN1), TRIM32, Rapsyn (RASPN), DOK7, Agrin (AGRN), COLQ, CHAT, acetylcholine receptors (CHRNE, CHRNA1, CHRNB1, CHRND), GFPT1, MUSK.

According to a particular embodiment, the sequence contained in the expression system of the invention does not encode a protein of the sarcoglycans family, especially the α-sarcoglycane, or more specifically the sequence described in the paper Mendell et al. (Annals of Neurology, Vol. 68, No 5, pp 629-638, 2010).

In another particular embodiment, the sequence contained in the expression system of the invention does not encode a dystrophin-like protein, including minidystrophin, and in particular that described in the paper Wang et al. (Gene Therapy, Vol. 15, No 22, pp 1489-1499, 2008).

More generally, this invention refers to any protein having therapeutic activity in a neuromuscular disease, for example whose mutation causes a disease in one or more target tissues, if its production from an expression system exhibits toxicity in at least one tissue, preferably a non-target tissue, especially the heart, and more exhaustively in at least one tissue from the following group: heart, liver, brain, lungs, kidney and smooth muscles.

According to the invention and advantageously, the expression system must allow the expression at a therapeutically acceptable level of the protein in the target tissues, preferably in the skeletal muscles and/or the peripheral nervous tissue. Moreover and according to another preferred embodiment, it must allow the expression at a toxically acceptable level of the protein in non-target tissues, particularly the heart.

In the context of this invention, the term "protein expression" may be understood as "protein production". Thus, the expression system must allow for both transcription and translation of the protein at the levels defined above.

The levels defined in the context of the invention, namely "therapeutically acceptable" and "toxically acceptable" are related to the amount of protein, as well as its activity.

The evaluation of the amount of protein produced in a given tissue can be carried out by immunodetection using an antibody directed against said protein, for example by Western blot or ELISA. Alternatively, the corresponding messenger RNAs may be quantified, for example by PCR or RT-PCR. This quantification can be performed on one sample of the tissue or on several samples. Thus and in the case where the target tissues are skeletal muscles, it may be carried out on a muscular type or several types of muscles (for example quadriceps, diaphragm, tibialis anterior, triceps, etc.).

In the context of the invention, the term "therapeutically acceptable level" refers to the fact that the protein produced from the expression system of the invention helps improve the pathological condition of the patient, particularly in terms of lifespan and quality of life. Thus and in connection with a disease affecting skeletal muscles, this involves improving the muscular condition of the subject affected by the disease or restoring a muscular phenotype similar to that of a healthy subject. As mentioned above, the muscular state, preferably defined by the strength, size, histology and function of the muscles, can be evaluated by one of the following methods: biopsy, measurement of the strength, muscle tone, volume, or mobility of muscles, clinical examination, medical imaging, biomarkers, etc.

Thus, the criteria that help assess a therapeutic benefit as regards skeletal muscles and that can be evaluated at different times after the treatment are in particular:
    increased life expectancy;
    increased muscle strength
    improved histology; and/or
    improved functionality of the diaphragm.

In the context of the invention, the term "toxically acceptable level" refers to the fact that the protein produced from the expression system of the invention does not cause significant alteration of the non-target tissue, especially histologically, physiologically and/or functionally. In particular, the expression of the protein may not be lethal. Advantageously, the amount of protein produced in the non-target tissue must not exceed the endogenous level of said protein in this tissue, in particular compared to a healthy subject. As already stated, the toxicity in a tissue can be evaluated histologically, physiologically and functionally. In the particular case of the heart and for illustrative purposes, any toxicity of a protein can be evaluated by a study of the morphology and the heart function, by clinical examination, electrophysiology, imaging, biomarkers, monitoring of the life expectancy or by histological analysis, including the detection of fibrosis and/or cellular infiltrates, for example by staining with sirius red or hematoxylin/eosin.

Advantageously, the level of efficacy and/or toxicity of the expression system according to the invention is evaluated in vivo in the animal, even more preferably in an animal having a defective copy of the gene encoding the protein and thus affected by the associated pathology.

Preferably, the expression system is administered systemically, for example by intravenous injection.

According to the invention and preferably, the expression system of the invention comprises at least one sequence that allows to:
    prevent the expression or decrease the level of expression of the protein in the non-target tissues, especially in those where the expression of the protein is toxic; and/or maintain the expression or increase the level of expression of the protein in the target tissue(s).

According to a particular embodiment, the invention relates to an expression system comprising at least one sequence that allows to:
prevent the expression or decrease the level of expression of the protein in tissues other than skeletal muscles and/or the peripheral nervous tissue, preferably those in which the expression of the protein is toxic; and/or
maintain the expression or increase the level of expression of the protein in skeletal muscles and/or the peripheral nervous tissue.

In the context of the invention, the terminology "prevent the expression" preferably refers to cases where, even in the absence of the said sequence, there is no expression, while the terminology "decrease the level of expression" refers to cases where the expression is decreased (or reduced) by the provision of said sequence.

Similarly, the terminology "maintain the expression" preferably refers to cases where, even in the absence of said sequence, there is a comparable level of expression, while the terminology "increase the level of expression" refers to cases where there is an increase in expression by the provision of said sequence.

In the context of the invention, there are at least three ways, which may be combined, to achieve the desired objective:
using a sequence capable of preventing the expression or reducing the level of expression of the protein in the non-target tissues, without reducing the level of expression in the target tissue(s);
the use of a promoter sequence capable of ensuring a high level of expression in the target tissue(s) and low or no expression in non-target tissues, especially in those where the expression of the protein appears toxic;
the use of a vector, preferably viral, having a suitable tropism, in this case higher for the target tissue(s) than for the non-target tissues, especially those where the expression of the protein appears toxic.

Suitably, an expression system of the invention comprises a promoter sequence governing the transcription of the sequence encoding the protein, preferably placed at 5' of the transgene and functionally linked thereto. Preferably, this ensures a therapeutically acceptable level of expression of the protein in target tissues, particularly in skeletal muscles.

This may include inducible or constitutive, natural or synthetic (artificial) promoters. Similarly, they can be of any origin, including human, of the same origin as the transgene or of another origin.

According to a first embodiment, the promoter sequence corresponds to a ubiquitous or non-selective promoter, that is to say a promoter with low tissue specificity and ensuring a broadly similar level of expression in different tissues, for both target and non target tissues. The following can be cited as examples: the cytomegalovirus promoter (pCMV), the Mtm1 promoter.

According to a particular embodiment, this refers to a promoter suitable for skeletal muscles and/or peripheral nerve tissue but which can be expressed in other tissues, especially in other muscles. The following can be cited as an example: the desmin promoter, preferably of sequence SEQ ID NO: 11, the skeletal alpha-actin promoter, the muscle creatine kinase (MCK) promoter, the C5-12 synthetic promoter, the synapsin I (Syn) promoter or the CK6 promoter. In relation to the skeletal muscles, others can also be cited: troponin, myogenic factor 5 (Myf5), myosin light chain 1/3 fast (MLC1/3f), myogenic differentiation 1 (MyoD1), myogenin (Myog), paired box gene 7 (Pax7), MEF2 promoters.

In connection with the peripheral nervous tissue, the P0 and MBP (Myelin Basic Protein) promoters can also be cited.

According to a preferred embodiment of the invention, the promoter sequence of the expression system is chosen for its promoter activity which differentiates between target and non-target tissues, in this case superior in the target tissues. In this case, this sequence helps increase the expression of the protein in the target tissues, preferably the skeletal muscles and/or peripheral nervous tissue, while preventing expression in the non-target tissues, particularly those in which the expression of the protein is toxic.

By way of example and in the case where the target tissue is skeletal muscle, the promoter is preferably a muscle-specific promoter. According to another advantageous characteristic, said promoter has low or no promoter activity in the non-target tissues, particularly the heart, enabling a toxically acceptable level of expression of the protein in these tissues.

According to a particular embodiment, said promoter sequence may correspond to the promoter of the calpain 3 gene, preferably of human origin, even more preferably of sequence SEQ ID NO: 12. Another suitable promoter sequence is that of the miRNA 206 (miR206), preferably of human origin, more preferably of sequence SEQ ID NO: 13.

Thus within the framework of the invention, it has been shown at least for Calpain 3, that an expression system comprising the sequence encoding said protein, placed under the control of the calpain 3 or miRNA 206 promoter, was capable of ensuring the expression at a therapeutically acceptable level of the protein in the skeletal muscles, and at a toxically acceptable level of the protein in the heart and liver.

In another aspect, the present invention therefore relates to an expression system comprising a sequence encoding a protein, placed under the control of a promoter having the sequence SEQ ID NO: 12 or SEQ ID NO: 13. Promoter sequences derived from the sequences SEQ ID NO: 12 and SEQ ID NO: 13 or corresponding to a fragment thereof but having a similar promoter activity, particularly in terms of tissue specificity and optionally effectiveness, are also covered under the present invention.

In case this promoter sequence does not allow expression at a toxically acceptable level of the protein in the non-target tissues, it is advantageously associated with a sequence having the function of reducing the level of expression of the protein in the non-target tissue, preferably in non-target tissues where the expression of the protein is toxic.

Thus and by way of example, in the case of both myotubularin and calpain 3, it was shown that the use of a desmin promoter presented cardiac toxicity. In contrast and in accordance with the invention, the use of a desmin promoter, preferably of sequence SEQ ID NO: 11, associated with at least one target sequence of the miRNA-208a, preferably of sequence SEQ ID NO: 10, allows both:
a therapeutically acceptable level of expression of the protein in the target tissue, preferably skeletal muscles;
a toxically acceptable level of expression of the protein in non-target tissues, preferably the heart, or the liver.

As already stated, said sequence is capable of preventing the expression or reducing the level of expression of the protein in non-target tissues, preferably in the non-target tissues where protein expression is toxic. This action may take place according to various mechanisms, particularly:
with regard to the level of transcription of the sequence encoding the protein;

with regard to transcripts resulting from the transcription of the sequence encoding the protein, e.g., via their degradation;

with regard to the translation of the transcripts into protein.

Such a sequence is preferably a target for a small RNA molecule selected from the following group:

microRNAs;
endogenous small interfering RNA or siRNAs;
small fragments of the transfer RNA (tRNA);
RNA of the intergenic regions;
Ribosomal RNA (rRNA);
Small nuclear RNA (snRNA);
Small nucleolar RNAs (snoRNA);
RNA interacting with piwi proteins (piRNA);
. . .

Advantageously, this sequence helps maintain the expression, or even increase the level of expression of the protein in the target tissue(s), preferably in the skeletal muscles.

Preferably, such a sequence is selected for its effectiveness in the non-target tissue wherein the expression of the protein is toxic. Since the effectiveness of this sequence can be variable depending on the tissues, it may be necessary to combine several of these sequences, chosen for their effectiveness in all target tissues where toxicity is proven.

According to a preferred embodiment, this sequence is a target sequence for a microRNA (miRNA). As known, such a judiciously chosen sequence helps to specifically suppress gene expression in selected tissues.

Thus and according to a particular embodiment, the expression system of the invention comprises a target sequence for a microRNA (miRNA) expressed or present in the non-target tissue(s) in which the expression of the protein is toxic, for example in the heart. Suitably, the quantity of this miRNA present in the target tissue, preferably skeletal muscles, is less than that present in the non-target tissue, or this miRNA may not even be expressed in the target tissue. According to a particular embodiment, the target miRNA is expressed specifically in the non-target target tissue, such as heart.

As is known to the person skilled in the art, the presence or level of expression, particularly in a given tissue, of a miRNA may be assessed by PCR, preferably by RT-PCR, or by Northern blot.

Different miRNAs now identified, as well as their target sequence and their tissue specificity, are known to those skilled in the art and are for example described in the document WO 2007/000668.

According to a particular embodiment, the expression system of the invention comprises the target sequence of the miRNA-208a (also noted miR208a, SEQ ID NO: 9). Preferably, this sequence, identical in humans, dogs and mice, has the sequence SEQ ID NO: 10 of 22 pb. Of course, any derived or truncated sequence recognised by the miRNA-208a may be implemented as part of the invention. Thus, it has been shown within the framework of the invention that the use of this target sequence, both in relation to the myotubularin and the calpain 3, makes it possible to solve the problem of their cardiac toxicity, or even hepatic toxicity in the case of calpain 3.

As already stated, a target sequence for a microRNA may be used alone or in combination with other sequences, advantageously target sequences for a microRNA, which may be identical or different. These sequences can be used in tandem or in opposite direction.

According to a preferred embodiment, particularly for the target sequence of the miRNA-208a, one (1) or more, particularly two (2) or four (4) sequences, may be implemented. Preferably, they are used in tandem, that is to say, all in the same direction. In cases where multiple target sequences are implemented, they may be separated by a DNA spacer of random sequence, in a manner known to those skilled in the art.

Preferably, in the case of a target sequence of a miRNA, particularly the miR208a, it is placed at 3' of the sequence encoding the protein, more advantageously inserted into the 3' UTR ("Untranslated Region") region of the expression system, preferably the cDNA encoding the protein. And even more preferably and where the expression system comprises a polyadenylation signal at 3' of the cDNA encoding the protein, this sequence is inserted between the stop codon of the open reading frame and the polyadenylation signal.

In the context of the invention, it has been demonstrated that at least one target sequence of the miRNA-208a was adapted to obtain a toxically acceptable level of the protein at least in the heart, in particular concerning myotubularin and calpain 3.

According to a particular embodiment, the expression system comprises:

a sequence encoding myotubularin placed under the control of a promoter, preferably desmin, even more preferably that of human desmin (SEQ ID NO: 11);
at least one target sequence of a miRNA expressed in the heart, preferably the miRNA-208a, preferably a single target sequence such as the sequence SEQ ID NO: 10.

In another particular form of embodiment, the expression system comprises:

a sequence encoding calpain 3 placed under the control of a promoter, preferably desmin, even more preferably that of human desmin (SEQ ID NO: 11), or that of calpain 3, even more preferably that of human calpain 3 (SEQ ID NO: 12), or that of miRNA206, even more preferably that of human miRNA206 (SEQ ID NO: 13);
at least one target sequence of a miRNA expressed in the heart, preferably the miRNA-208a, even more preferably two target sequences in tandem.

Thus, different types of sequences detailed above may be combined in the same expression system.

According to the invention, an expression system or expression cassette comprises the elements necessary for the expression of the transgene present. In addition to sequences such as those defined above to ensure and to modulate transgene expression, such a system may include other sequences such as:

A polyadenylation signal, for example polyA of the SV40 or human haemoglobin, preferably inserted at 3' of the coding sequence, or 3' of the target sequence of the miRNA;
Sequences to stabilise the transcripts, such as intron 1 of human hemoglobin;
Enhancer sequences;
. . .

An expression system according to the invention can be introduced in a cell, a tissue or a body, particularly in humans. In a manner known to those skilled in the art, the introduction can be done ex vivo or in vivo, for example by transfection or transduction. According to another aspect, the present invention therefore encompasses a cell or a tissue, preferably of human origin, comprising an expression system of the invention.

The expression system according to the invention, in this case an isolated nucleic acid, can be administered in a subject, namely in the form of a naked DNA. To facilitate the introduction of this nucleic acid in the cells, it can be combined with different chemical means such as colloidal disperse systems (macromolecular complex, nanocapsules, microspheres, beads) or lipid-based systems (oil-in-water emulsions, micelles, liposomes).

Alternatively and according to another preferred embodiment, the expression system of the invention comprises a plasmid or a vector. Advantageously, such a vector is a viral vector. Viral vectors commonly used in gene therapy in mammals, including humans, are known to those skilled in the art. Such viral vectors are preferably chosen from the following list: vector derived from the herpes virus, baculovirus vector, lentiviral vector, retroviral vector, adenoviral vector and adeno-associated viral vector (AAV).

Preferably, it is an adeno-associated viral vector (AAV) corresponding to natural serotypes (AAV1, AAV2, AAV3, AAV4, AAV5, AAV6, AAV7, AAV8 and AAV9), variants thereof or artificial serotypes. In a manner known to those skilled in the art, chimeric AAV vectors may also be implemented.

Preferably, the expression system of the invention is inserted between two ITR ("Inverted Terminal Repeat") sequences of the AAV vector.

In connection with a systemic administration to which the expression system of the invention is fully applicable, AAV vectors of serotype 8 or 9 are particularly preferred. This may for example include AAV2/8 or AAV2/9 vectors.

In a manner known to those skilled in the art, recombinant virus particles can be obtained, for example by tri-transfection of HEK 293 cells or by the baculovirus system. The vector titres are conventionally expressed as viral genomes per milliliter (vg/ml).

According to a preferred embodiment, the expression system of the invention includes a vector having a suitable tropism, in this case higher for the target tissue(s) than for the non-target tissues, especially those where the expression of the protein appears toxic. It can be an AAV vector containing a capsid selected for minimum or no targeting/transducing the non-target tissues such as the heart or to specifically target/transduce target tissues, especially skeletal muscles.

As is apparent from the above, the expression systems according to the invention, especially in the form of recombinant AAV vectors or recombinant viral particles, have obvious applications, especially in the field of therapeutics.

Thus and according to another aspect, the invention relates to the use of the expression system described as a medicine. In other words, a pharmaceutical composition comprising such an expression system is also covered. Suitably, it may further comprise a pharmaceutically acceptable and inert carrier, preferably adapted for systemic administration, e.g., intravenous administration. Various excipients, stabilisers, and other known suitable compounds known to those skilled in the art can be added to such a composition.

The present invention has demonstrated the benefit of the expression system described in cases where administration is not done locally in the target tissues, but instead generally in the whole body, resulting in its delivery in the non-target tissues.

Thus, and preferably, an expression system according to the invention is administered by one of the following routes: enteral, parenteral, oral, intravenous, intraarterial and by inhalation.

Preferably, it is a systemic administration, and more preferably an intravenous injection. Note that a systemic administration may be performed near a treatment area, for example near a skeletal muscle.

According to a particular form of embodiment, it is not a loco-regional administration. More specifically, the following can thus be excluded: an intravascular, particularly intravenous, injection (performed under pressure and in the presence of a tourniquet, close to the target muscle), as described for example by Petrov et al. (Methods Mol Biol 2011; 709: 277-86), or an intra-arterial injection (catheter in an artery and venous clamping near the artery, upstream, to prevent diffusion) as described for example by Gonin et al. (J Gene Med 2005; 7: 782-791).

When the composition of the invention is to be injected, it is preferably in liquid form. The active concentration, in this case the expression system of the invention, the quantity to be injected and the frequency of injections are determined by a person skilled in the art. A single administration may be sufficient. A therapeutic effect is preferably observed for a period of at least 1 month, 3 months, 6 months, 1 year, 5 years or more.

Such medicines are intended for gene therapy, particularly for the treatment of neuromuscular disorders and more particularly diseases mainly affecting skeletal muscles (myopathy). More generally, the invention helps improve muscle function in a subject.

Patients to be treated are preferably mammals, particularly humans.

A disease particularly referred to in the context of the invention is centronuclear myopathy, more precisely X-linked myotubular myopathy (XLMTM). Furthermore, other centronuclear myopathy and neuromuscular diseases associated with myotubularin, such as some forms of the Charcot-Marie-Tooth disease, can be treated.

Type 2A limb-girdle dystrophy (LGMD2A) may also be treated with an expression system of the invention.

More generally, a non-exhaustive list of diseases covered by this invention is as follows: congenital muscular dystrophy with selenoprotein N deficiency, congenital muscular dystrophy with primary merosin deficiency, Ullrich congenital muscular dystrophy, Duchenne (DMD) or Becker (BMD) muscular dystrophy, central core congenital myopathy, multi-minicore congenital myopathy, centronuclear autosomal myopathy, myopathy with fibre dysproportion, nemaline myopathy, congenital myasthenic syndromes, other neuromuscular diseases associated with myotubularin, Type 2B or 2D limb-girdle dystrophy, miyoshi distal myopathy, dysferlinopathies, sarcoglycanopathies.

According to a particular form of embodiment, the pathology is not the Duchenne (DMD) or the Becker (BMD) muscular dystrophy or even the LGMD2D.

Therefore, both an improvement of the condition, and thus the quality of life and longevity of the patient are expected of the medicine according to the invention, while avoiding potential side effects in other tissues of such a treatment.

As will be demonstrated by way of example, the present invention has demonstrated the potential cardiac toxicity of the gene therapy treatments for muscle diseases and offers technical solutions to overcome this problem.

EXPERIMENTAL EXAMPLES

The invention and the advantages resulting from it will be better understood with the examples of realisation given below and with the help of the figures annexed. However, these are not exhaustive.

The present invention is illustrated in connection with the myotubularin (MTM1) and calpain 3 (CAPN3) gene. However, the strategy described can be applied to any transgene encoding a protein of interest in the skeletal muscles whose cardiac toxicity is demonstrated.

FIG. 1: Diagram of the vector constructs:

A/ Mtm1 expression cassette, devoid of target sequences for miRNA-208a;

B/ expression cassette containing 1, 2 or 4 target sequences for miRNA-208a (box) at 3' of the Mtm1 gene.

Figure 2:
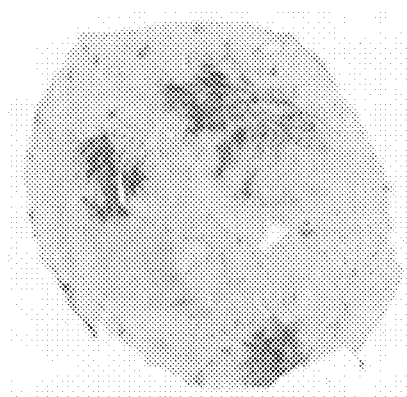

FIG. 2: Cross section of the heart of a XLMTM mouse treated with AAV-pDES-Mtm1 vector. Fibrosis areas were found in red owing to the sirius red staining.

FIG. 3:

Top: distribution of the vector in skeletal muscles (tibialis anterior=TA; quadriceps=QUA; triceps=TRI) and in the heart of a wild mouse (WT), 1 month after the intravenous administration of vectors (vg/diploid genome).

Bottom: level of MTM1 protein in skeletal muscles and the heart of a wild mouse (WT), one month after administration of the vectors. The values indicate the multiplication rate in relation to the endogenous levels. As controls, mice were injected with either PBS or empty AAV8 vector (AAV-MCS).

Figure 4:
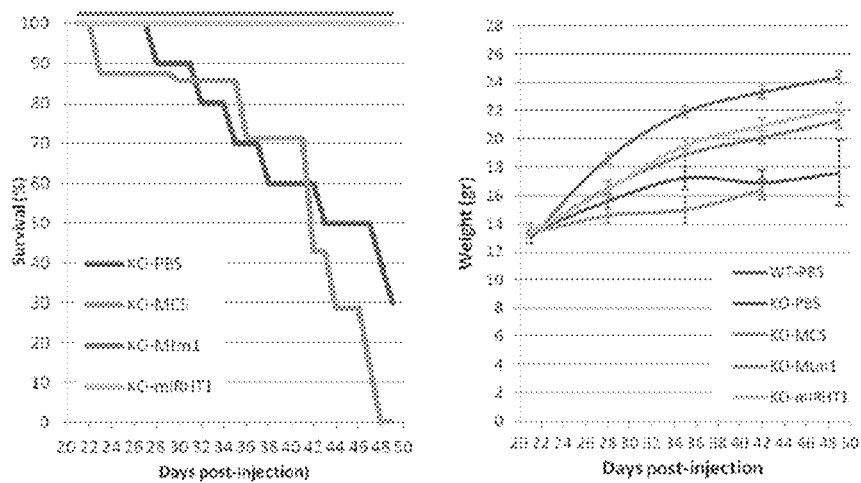

FIG. 4: Survival curve (left) and body mass curve (right) of Mtm1 KO mice ("Knock Out") injected with either PBS, AAV8-Des-MCS, AAV8-Des-Mtm1 or AAV8-Des-Mtm1-miRHT1. Wild mice (WT) received PBS as a control.

Figure 5:
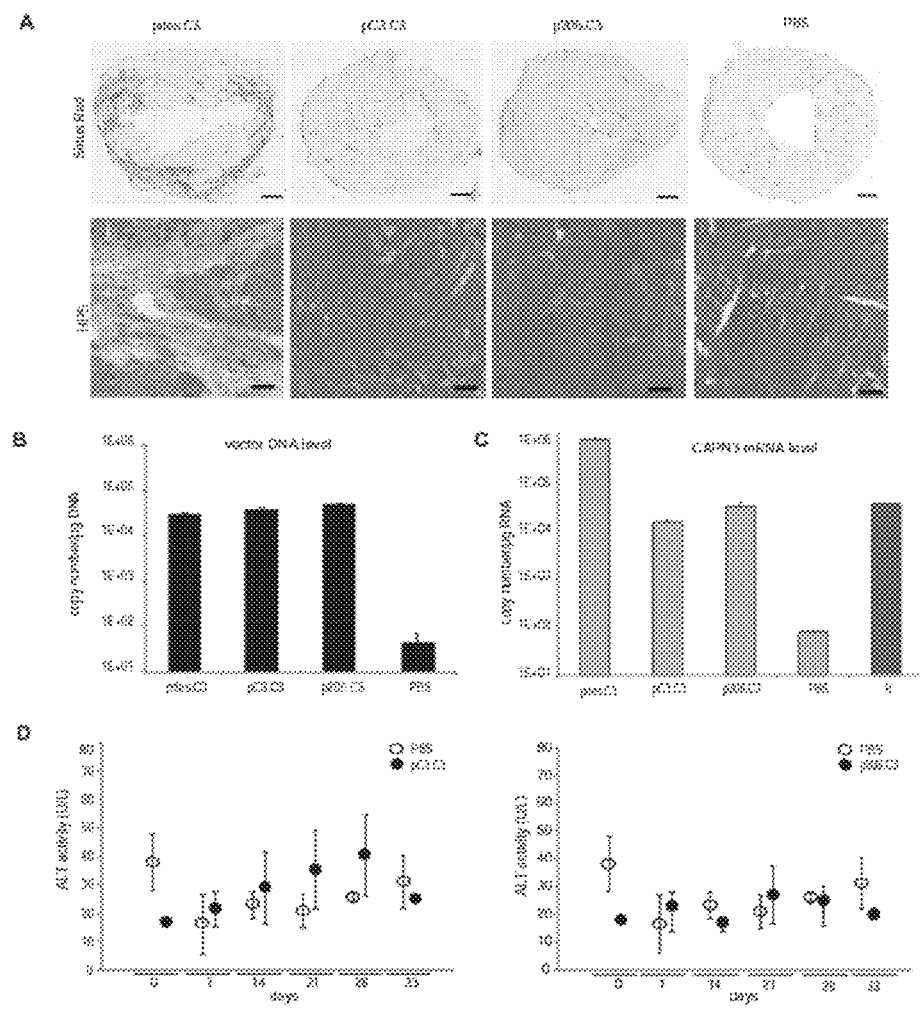

FIG. 5: Analysis of promoter activity of CAPN3 and miR-206 in vivo:

A/ Histological analysis of the heart muscle after injection of PBS or the vectors AAV2/9-desm-CAPN3 (pdes.C3), AAV2/9-pC3-CAPN3 (pC3.C3), AAV2/9-pmiR206-CAPN3 (p206.C3) and Sirius red staining (top, scale=500 μm) or Hematoxylin Phloxine Saffron (HPS) (bottom, scale=100 μm).

B/ Evaluation of the vector DNA level by qPCR in the heart of WT wild mice after injection.

C/ Evaluation of the CAPN3 mRNA level by qPCR in the heart of WT wild mice after injection. The line "H" corresponds to the CAPN3 endogenous mRNA level in the heart of WT wild mice.

D/ Analysis of serum enzymes. The alanine aminotransferase tests (ALT) were carried out on sera of WT mice treated with pC3.C3 to the left, or p206.C3 to the right. The standard deviation and mean (SEM) for each condition are indicated by a circle and a vertical bar, respectively.

Figure 6:
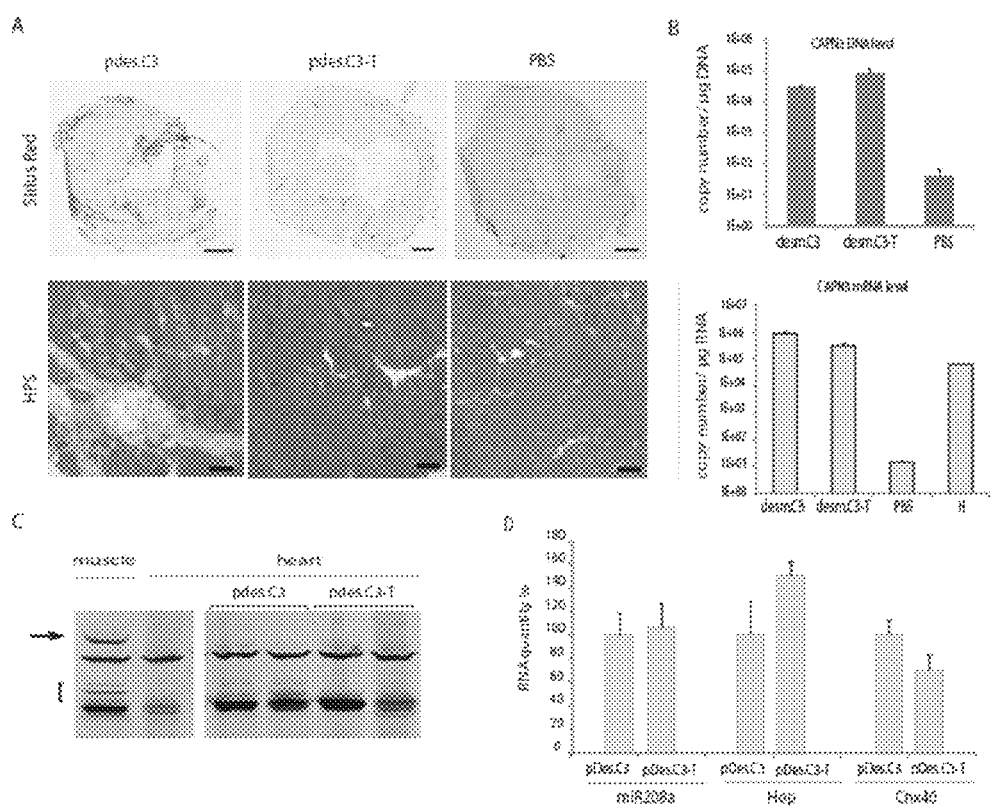

FIG. 6: Analysis of the activity of miR-208aT in vivo:

A/ Histological analysis of the heart muscle, 35 days after injection of PBS or identical doses of the vectors AAV2/9-desm-CAPN3 (pdes.C3) or AAV2/9-desmin-CAPN3-miR208aT (pdes.C3-T) and Sirius red staining (top, scale=500 μm) or HPS (bottom, scale=100 μm).

B/ Evaluation of the vector DNA level by qPCR in the heart of WT wild mice after injection (top) and the mRNA level of CAPN3 transgene (bottom). The line "H" corresponds to the CAPN3 endogenous mRNA level in the heart of WT wild mice.

C/ Analysis of the expression of calpain 3 by Western blot in the skeletal muscle and heart of WT mice injected with PBS or the vectors AAV2/9-desmin-CAPN3 (pdes.C3) or AAV2/9-desm-CAPN3-miR208aT (pdes.C3-T). The entire protein is indicated by an arrow and its cleavage products (60, 58 and 55 kDa) by a hook.

D/ Quantification of mRNA levels of miR-208a (miR208a), HOP (Hop) and connexin 40 (Cnx40) in the heart of WT mice injected with AAV2/9-desmin-CAPN3 (pdes.C3) or AAV2/9 desmin-CAPN3-miR208aT (pdes.C3-T). The quantity of RNA in the pdes.C3-T condition is given as a percentage of the RNA level in the pdes.C3 condition.

Figure 7:
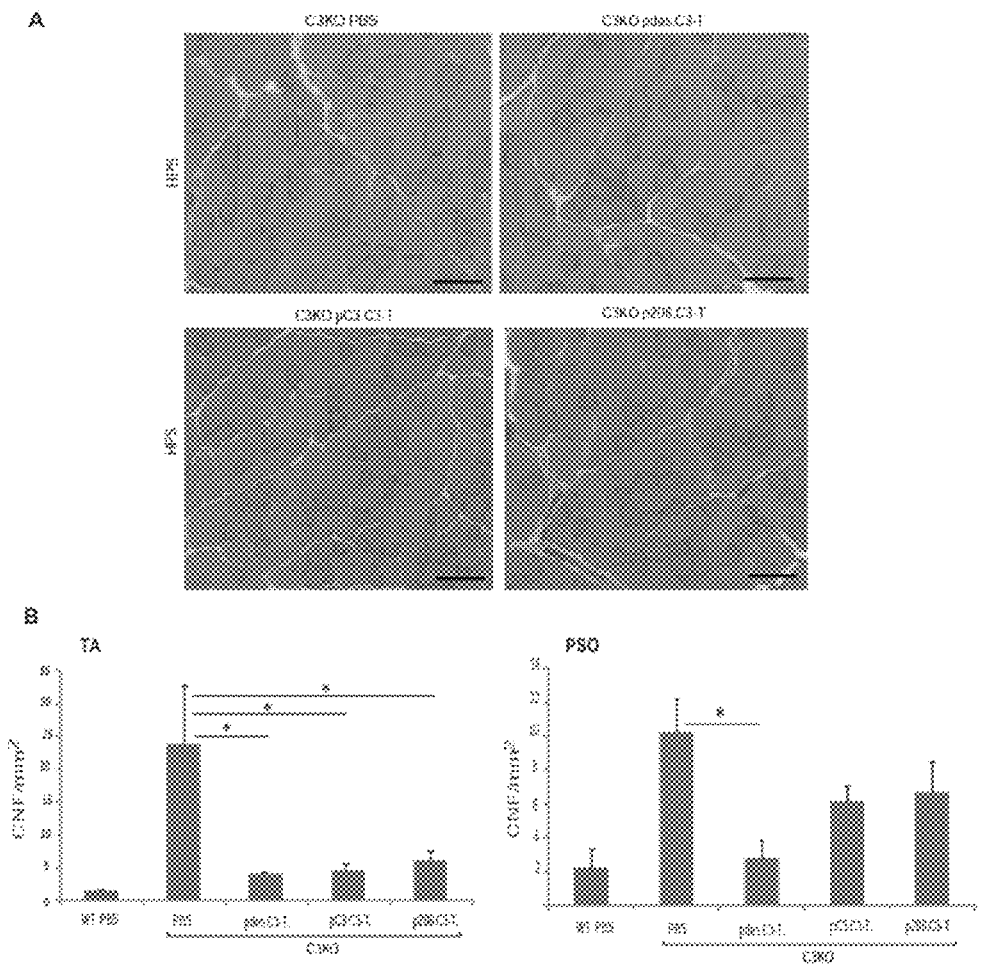

FIG. 7: Histological analysis of the efficiency of transfer of calpain 3 in skeletal muscles of mice deficient in calpain 3:

A/ Transverse sections of the TA muscles of C3KO mice were stained with the HPS, 4 months after injection either with PBS or vectors ($1.2 \times 10^{13}$ vg/kg) AAV2/9-desmin-CAPN3-miR208aT (pdes.C3-T), AAV2/9-PC3-CAPN3-miR208aT (pC3.C3-T), AAV2/9-pmiR206-CAPN3-miR208aT (P206.C3-T). Scale=100 μm.

B/ Number of centronuclear fibres ($CNF/mm^2$) measured in the stained sections with the HPS in TA (left) and PSO (right) muscles of C3KO mice injected either with PBS or vectors ($1.2 \times 10^{13}$ vg/kg) AAV2/9-desmin-CAPN3-miR208aT (pdes.C3-T) AAV2/9-PC3-CAPN3-miR208aT (pC3.C3-T), AAV2/9-pmiR206-CAPN3-miR208aT (p206.C3-T). A difference with a P value<0.05 is indicated by an asterisk. TA: tibialis anterior; PSO: Psoas muscle.

I) MATERIAL AND METHODS

1) Generation of Recombinant AAV Vectors:

The vector rAAV-Des-Mtm1 was constructed by cloning the open reading frame of the murine Mtm1 gene (SEQ ID NO: 14) downstream of the human desmin promoter (SEQ ID NO: 11) in a vector serotype 2 AAV. Target sequences (1, 2 or 4 sequences, miRHT1, miRTH2 and miRHT4 respectively) of the miRNA-208a of 22 pb (SEQ ID NO: 10), each separated by DNA spacers, have been added in the 3'UTR region of the Mtm1 cDNA. An empty vector (rAAV-Des-MCS) was also generated as a control. Recombinant viral particles of serotype 8 (AAV8) were obtained using a tri-transfection protocol of the HEK 293 cells as described previously (15). The vector titres are expressed in terms of viral genomes per ml (vg/ml).

Similarly, the vector rAAV-desm-CAPN3 (or AAV-desmin-CAPN3 or AAV-pDes-CAPN3) was constructed using the cDNA of human calpain 3 (SEQ ID NO: 8) under the control of the human desmin promoter (SEQ ID NO: 11). RAAV-PC3-CAPN3 and rAAV-pmiR206-CAPN3 vectors were obtained by replacing this promoter by the promoter region of the human calpain 3 (SEQ ID NO: 12) or that of the miARN206 (SEQ ID NO: 13), respectively. The vectors AAV-desm-CAPN3-miR208aT, AAV-PC3-CAPN3-miR208aT and AAV-pmiR206-CAPN3-miR208aT were obtained by adding 2 target sequences for the miARN208a (SEQ ID NO: 9) in tandem (miR208aT), at 3' of the calpain gene 3. Recombinant viral particles of serotype 1 (AAV1), 8 (AAV8) and/or 9 (AAV9) were produced.

2) In Vivo Experiments:

The mice were treated according to the French and European legislation regarding animal testing. In this study, WT C57Bl/6 wild mice (Charles River Laboratories) and a mouse strain constitutively inactivated for myotubularin (knockout) KO-Mtm1, also called BS53d4-129pas, were used. For calpain 3, the C3KO murine model, described by Laure et al. (Febs J., 2010, 277: 4322-4337), was used.

Recombinant vectors, as per the indicated doses were injected into the tail vein of the mice as indicated (aged 3 weeks to 2 months). An equivalent volume of saline buffer (PBS) was administered as a control. The clinical status and animal weight were monitored weekly for WT animals and three times per week for the mutant mice. The mice were sacrificed at the indicated times.

3) Western Blot:

Muscles frozen in isopentane were cut in cross-sections of 30 μm and lysed on ice in a buffer containing 150 mM NaCl, 10 mM Tris HCl (pH 7.4), 1 mM EGTA, 1 mM EDTA, 100 mM sodium fluoride, 4 mM sodium pyrophosphate, 2 mM sodium orthovanadate, 1% Triton X100 and 0.5% IGEPAL supplemented with a complete cocktail of protease inhibitors (Roche). The muscle extracts were incubated for 1 h and centrifuged at 4° C. at 12,000×g for 30 min. The protein concentrations in the supernatant were determined using the Bio-Rad "protein assay kit". Proteins were subjected to migration to SDS-PAGE and, after transfer to a nitrocellulose membrane, incubated with polyclonal antibodies directed against the myotubularin (p2348 [15]) and GAPDH (#MAB374, Millipore). The protein bands were viewed by infrared fluorescence using the "Odyssey Imaging System" (LICOR Biotechnology Inc.) and quantified using the program "Odyssey Infrared Imaging System Software" (software application, version 1.2, 2003).

For detection of calpain 3, a similar protocol was used:

The muscles were homogenized by FastPrep using the lysis buffer according to [20 mM Tris (pH 7.5), 150 mM NaCl, 2 mM EGTA, 0.1% Triton X-100, 2 mM E64 (Sigma)] and protease inhibitors (Complete Mini protease inhibitor cocktail; Roche Applied Science, 25 μl per mg of tissue). The samples were treated with 250 U/100 μl of Benzonase (Calbiochem) for 30 min at 4° C. to digest the DNA. The muscle lysates were mixed with the load buffer [NuPage LDS (Invitrogen), TNT 3M (Sigma)], denatured for 10 minutes at 70° C. and centrifuged briefly. The supernatants were separated by polyacrylamide gel NuPAGE Bis-Tris in 4-12% gradient (Invitrogen). After the transfer, the membranes were hybridised with antibodies against calpain 3 (mouse monoclonal antibody, Novocastra NCL-CALP-12A2, 1/200 dilution), at 4° C. overnight or at room temperature for 2-3 hours. Finally, the membranes were incubated with IRDye® in order to be revealed on the Odyssey infrared scanner (LI-COR Biosciences, Lincoln, Nebr., USA).

4) PCR:

4-1—Myotubularin:

The isolation of DNA from the muscles was performed using the "Gentra Puregene Tissue Kit" (Qiagen), in accordance with the manufacturer's instructions. The total DNA concentration was determined using a ND-8000 Nanodrop spectrophotometer (Nanodrop Technologies, France), and 80 ng of DNA for each sample was used as matrix for the PCR in real time. The Taqman real-time PCR was performed on each sample for both a part of the skeleton common to the rAAV2/X vector to identify copies of the viral genome, and the murine gene of the titin, to standardise the number of murine genomes present in each sample. The primers used for amplification of the rAAV vectors were: 5'-CTCCAT-CACTAGGGGTTCCTTG-3' (forward; SEQ ID NO: 15), 5'-GTAGATAAGTAGCATGGC-3' (reverse; SEQ ID NO: 16). The MGB probes were double-labelled (FAM-NFQ): 5'-TAGTTAATGATTAACCC-3' (probe; SEQ ID NO: 17). Primers and a probe used for the titin were: 5'-AAAAC-GAGCAGTGACGTGAGC-3' (forward; SEQ ID NO: 18), 5'-TTCAGTCATGCTGCTAGCGC-3' (reverse; SEQ ID NO: 19), and 5'-TGCACGGAAGCGTCTCGTCTCAGTC-3' (probe; SEQ ID NO: 20) (Applied Biosystem). The amplifications of the titin were performed using 80 ng of DNA diluted in an "Absolute QPCR ROX Mix" (Thermo Fischer Scientific), 0.1 μM of Taqman probes and 0.2 μM of primers (forward and reverse), in a final volume of 25 μM.

The cycle conditions consisted of: an activation step for the Thermo-Start DNA polymerase at 95° C. for 15 min, followed by 40 two-step cycles, 15 seconds of denaturation at 95° C. and 60 seconds of hybridisation and extension at 60° C. The amplification of the rAAVs was performed using 0.1 μM of Taqman probes, 0.3 μM of reverse primer and 0.05 μM of forward primer in a final volume of 25 μl. The cycle conditions consisted of: an activation step for the Thermo-Start DNA polymerase at 95° C. for 15 min, followed by 40 two-step cycles, 15 seconds of denaturation at 95° C. and 60 seconds of hybridisation and extension at 54° C. The PCR was performed on a 7900 HT thermocycler (Applied Biosystem). A standard dilution series of a plasmid containing the sequences of a rAAV skeleton and the titin was used in each PCR plate in real time as control of the number of copies. All samples and controls were duplicated. The data are expressed as number of copies of the viral genome per diploid genome.

4-2—Calpain 3:

The muscles were extracted using the Trizol method (Invitrogen). During extraction, a sample fraction was preserved for DNA extraction for quantification by quantitative PCR. The total RNA was extracted from the remaining extract treated with the "DNA-Free" kit (Ambion) to remove residual DNA.

For quantification of the expression of endogenous microRNAs, a total of 20 ng RNA were subjected to a reverse transcription using the "reverse transcription TaqMan MicroRNA" kit (Applied Biosystems) and analysed by the microRNA ID511 Taqman assay for miR-208a (Applied Biosystems). The standardisation of the samples was carried out with the expression of snoRNA202 with test ID1232 (Applied Biosystems).

For the amplification of mRNAs of the endogenous or transgenic calpain 3, one μg of RNA was reverse transcribed using random hexamers and oligodT and the cDNA Verso kit (Abgene) or "RevertAid H Minus First Strand cDNA Synthesis" kit (Fermentas). The real-time PCR was performed using the TaqMant method applying the ABI PRISM 7700 (Applied Biosystems) system and the "Absolute QPCR Rox Mix" solution (ABgene) with the help of the primer pairs (.f and .r) and Taqman probe (.p) below: for the quantification of transgenic calpain: CAPN3sfr.f (SEQ ID NO: 21) 5'_CGCCTCCAAGGCCCGT_3'; CAPN3sfr.r (SEQ ID NO: 22) 5'_GGCGGAAGCGCTGGCT_3'; MGBTUCAPN3.p (SEQ ID NO: 23) 5'_CTACAT-CAACATGAGAGAGGT_3; for quantification of human calpain: CAPN3.f (SEQ ID NO: 24) 5'_CGCCTC-CAAGGCCAGG_3', CAPN3.r (SEQ ID NO: 25) 5'_GGCGGAAGCGCTGGGA_3 et CAPN3.p (SEQ ID NO: 26) 5'_TACATCAACATGCGGGAGGT_3. A serial dilution of a control RNA was used in each experiment and treated with the experimental samples to avoid the variability in the efficiency of the cDNA preparation and the PCR in order to be able to compare the different experiments. This RNA was prepared by an in vitro transcription reaction from a plasmid carrying a cDNA calpain 3 mutated and amplifiable by all the pairs of primers.

The analysis of the expression of the connexin 40 and HOP was performed using the TaqMan® Gene Expression tests (Applied Biosystens) given below: for Cnx40; Gja-5 [Mus Musculus]: Mm00433619_s1 and hop: HOP homeobox [Mus musculus]: Mm00558630_m1. The qRT-PCR results are expressed in arbitrary units related to the expression of the ubiquitous ribosomal phosphoprotein acid murine gene (P0 G1: 15029771; MH181PO.F (SEQ ID NO: 27): 5'_CTCCAAGCAGATGCAGCAGA_3'/M267PO.R (SEQ ID NO: 28): 5'_ACCATGATGCGCAAGGCTAT_3'/ M225PO.p (SEQ ID NO: 29): 5 <<_CCGTGGTGCT-GATGGGCAAGAA_3').

5) Histology:

Cross cryosections (8 μm thickness) of the cardiac, hepatic or skeletal muscles were stained with hematoxylin eosin (HE), sirius red or Hematoxylin Phloxine Saffron (HFS) using standard protocols.

The sections were mounted with the Eukitt medium (LABONORD). The digital images were captured using a CCD camera (Sony). The morphometric analyses of the skeletal muscles to define the number of centronuclear fibres (CNF/mm$^2$) were performed using the Histolab software (Microvision, Evry).

6) Measurement of ALT Activity:

Blood samples were collected without coagulation. After centrifugation (8000 g, 10 min, 4° C.), the sera were analysed using the VITROS DT60 device (Ortho Clinical Diagnostics, UK) using the "Vitros ALT DT slides" cassettes for the determination of the alanine aminotransferase (ALT) rate.

II) RESULTS

A—Myotubularin

1) Cardiac Toxicity of the Construction AAV-pDES-Mtm1:

The beneficial effect of a single intramuscular injection of the myotubularin (Mtm1) gene under the control of the CMV promoter in a vector AAV2/1 was known from the paper Buj-Bello et al. [15]

A gene therapy approach by systemic route in Mtm1 knockout mice was attempted and it has been shown that administration of an AAV8 vector (rAAV-Des-Mtm1) expressing myotubularin under the control of human desmin promoter (FIG. 1A) in a mutant mouse led to a prolonged life of at least 6 months, a strong improvement in the pathology in the striated muscles throughout the body including the diaphragm, and a standardised motor activity (results not shown).

However, following systemic administration of the vector AAV8-DES-Mtm1 in Mtm1 KO mice, it was observed that the level of myotubularin protein was very high in the heart compared to the skeletal muscles (results not shown). In addition, the presence of inflammatory infiltrates and fibrosis in the heart of XLMTM mice treated with AAV at different times following the viral injection (FIG. 2) was noted.

2) Developments of Expression Systems without Cardiac Toxicity

Given the difficulty to predict the biodistribution and transgene expression from a vector AAV8 after systemic administration, particularly in humans, new vectors carrying regulatory sequences increasing the muscle specificity have been developed in order to avoid potential side effects affecting the heart.

Three viral constructs (rAAV-Des-Mtm1-miRHT1; rAAV-Des-Mtm1-miRHT2 and rAAV-Des-MTM1-miRHT4) were developed, as shown in FIG. 1B, comprising respectively 1, 2 or 4 target sequences for the miRNA-208a. This sequence has the SEQ ID NO: 10 and consists of 22 base pairs. Remarkably, this sequence is conserved in humans, dogs and mice.

3) Muscle and Heart Production of MTM1 after Injection in a WT Mouse

In order to select the expression vector that is most suitable for MTM1, a single dose of 3×10$^{13}$ viral genomes (vg)/kg of these vectors was administered in the tail vein of wild-type mice aged 3 weeks. An empty vector (AAV-Des-MCS) and PBS ("Phosphate Buffered Saline") were used as internal controls.

Figure 3:
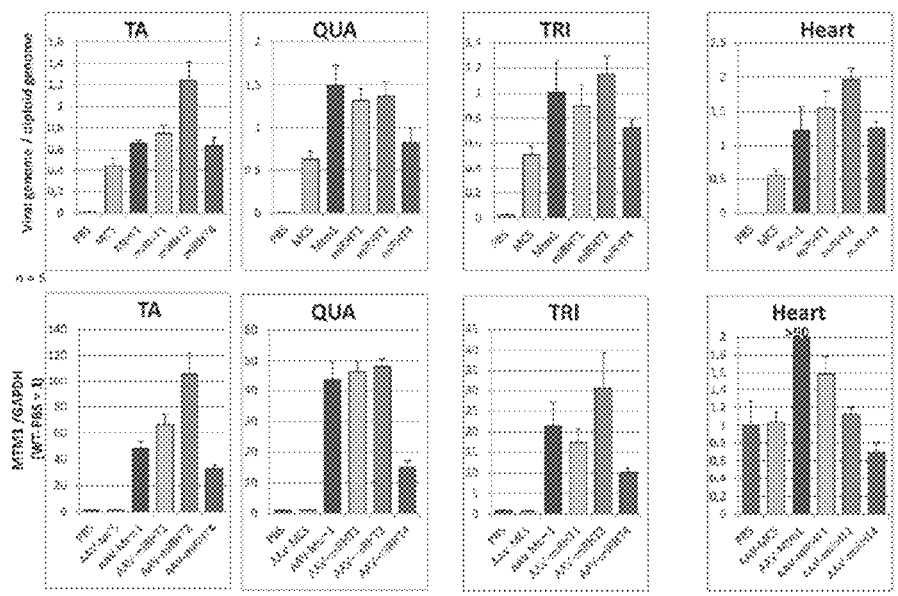

The vector distribution and protein level in myotubularin in the heart and in different skeletal muscles (anterior tibial=TA; quadriceps=QUA, triceps=TRI) were assessed 1 month after the injection. Western blot results showed that these vectors are able to decrease the level of myotubularin produced from vectors specifically in the heart. In addition, a single target sequence of the miRNA208a is sufficient to reduce expression in this tissue (FIG. 3 and Table 1).

TABLE 1

Semi-quantitative quantification of the MTM1 protein in the skeletal muscles and the heart, one month after the delivery of a vector in a WT mouse.

|  |  | PBS | Mtm1 | miRHT1 | miRHT2 | miRHT4 |
|---|---|---|---|---|---|---|
| Skeletal | TA | 1 | 50 | 70 | 100 | 30 |
| muscles | QUA | 1 | 45 | 45 | 50 | 15 |
|  | TRI | 1 | 20 | 17 | 30 | 10 |
| Heart |  | 1 | >90 | 1.6 | 1.1 | 0.7 |

4) Validation of the Vector Construction after Injecting an Mtm1 Mutated Mouse

Based on previous results, the construct rAAV-Des-Mtm1-miRHT1 was selected for further experiments. WT wild mice mutated in the MTM1 gene (KO for "Knock Out") received 3×10$^{13}$ vg/kg of AAV-Des-Mtm1, rAAV-Des-Mtm1-miRHT1 and rAAV-Des-MCS, respectively, or PBS at the age of 3 weeks, and were clinically monitored for 1 month.

All mutant mice that received AAV8-Des-Mtm1-miRHT1 survived until the end of the study, with a growth curve similar to that of KO mice treated with AAV8-Des-Mtm1 showing that the inclusion of the miRHT1 sequence does not affect the therapeutic efficacy of the transgene (FIG. 4).

The histology of the heart of WT and KO mice was analysed one month after treatment, with hematoxylin-eosin and Sirius red staining. Fibrotic areas were observed in the heart of 7 KO mice out of 9 treated with 9-AAV8-Des-Mtm1, but not in the KO mice treated with AAV8-Des-Mtm1-miRHT1 (n=10). The administration of the vector AAV8-Des-Mtm1 did not cause fibrosis in WT animals 1 month after injection (n=8).

In conclusion, these results indicate that the inclusion of a single target sequence of miARN208a is sufficient to reduce the cardiac toxicity of an AAV8-Des-Mtm1 construct.

Similar experiments were conducted with regard to calpain 3 (CAPN3):

B—Calpain 3

The paper Bartoli et al. (Molecular Therapy, 2006, Vol. 13, No. 2, 250-259) indicates a beneficial effect and non-toxicity of AAV type of constructs carrying the calpain 3 gene under the control of muscle-specific promoters, after intramuscular or local administration. However, the experiments carried out in connection with the invention have revealed toxicity in such constructs after systemic administration:

1) Cardiac Toxicity of AAV-desm-CAPN3 Constructs:

The condition of WT mice was monitored, following intravenous injection of different constructs, and is presented in Table 2 below:

TABLE 2

Consequences of intravenous injections of different AAVs at different doses

| Serotype | Dose (vg/kg) | Number of deaths | Histological appearance of the heart after 35 days |
|---|---|---|---|
| AAV9 | $4.0 \times 10^{11}$ | 0/3 | fibrosis |
| " | $1.0 \times 10^{12}$ | 0/9 | fibrosis |
| " | $1.6 \times 10^{13}$ | 5/7 | fibrosis |
| " | $4.3 \times 10^{13}$ | 2/6 | fibrosis |
| AAV8 | $7.0 \times 10^{12}$ | 2/4 | fibrosis |
| AAV1 | $1.6 \times 10^{13}$ | 0/3 | fibrosis |

For all tested AAVs, a destruction of heart tissue is observed in case of systemic administration, excluding the use for therapeutic purposes of these gene expression systems.

2) Reduction of Cardiac Toxicity of the Constructs AAV-desm-CAPN3 by Replacing the Promoter:

Two vectors were constructed by exchanging the desmin promoter with that of CAPN3(AAV2/9-pC3-CAPN3) or miR-206 (AAV2/9-pmiR206-CAPN3). After viral preparation of vectors, the in vivo consequences of the changes introduced by intravenous injection ($6 \times 10^{12}$ vg/kg) were analysed in C57BL/6 mice (WT) aged 2 months.

35 days after injection, no cardiac fibrosis was observed in mice treated with the vectors AAV2/9-pC3-CAPN3 and AAV2/9-pmiR206-CAPN3, unlike the mice injected with AAV2/9-desm-CAPN3 (FIG. 5A), in spite of similar levels of transduction (FIG. 5B). The level of mRNA of the CAPN3 transgene in the heart of mice treated with AAV2/9-desm-CAPN3 was about 15 times higher than the endogenous level (FIG. 5C), while it remained lower for mice treated with AAV2/9-pC3-CAPN3 and AAV2/9-pmiR206-CAPN3 (13% and 30%, respectively, FIG. 5C), which correlates the non-toxic effect of these two vectors. Moreover, it was verified that these two promoters showed no hepatic toxicity by measuring for about 5 weeks the level of alanine aminotransferase activity (ALT) in WT mice injected with $10^{13}$ vg/kg. No increase in enzyme activity was observed in animals injected compared to those injected with PBS (FIG. 5D).

Finally, the promoters CAPN3 and miR-206 reduce the cardiac toxicity of the transgene CAPN3 without causing liver toxicity.

3) Reduction of the Cardiac Toxicity of the AAV-desm-CAPN3 Constructs by Addition of Two Target Sequences of miR208a:

Two target sequences of MiARN208a (SEQ ID NO: 10) were cloned in tandem in a miR208aT cassette. This was then inserted into the 3'UTR area of the construct AAV2/9-desm-CAPN3 to produce the construct AAV2/9-desm-CAPN3-miR208aT.

After injecting a dose of $6 \times 10^{12}$ vg/kg, no cardiac fibrosis was observed in the treated mice, unlike the mice injected with AAV2/9-desm-CAPN3 (FIG. 6A), despite a similar level of transduction and an mRNA level 5 times higher compared to the endogenous level of calpain 3 in the heart (FIG. 6B). As regards the protein level, calpain 3 is not normally expressed in the myocardium and is not detected (FIG. 6C). In the WT mice injected with AAV2/9-desm-CAPN3, the whole protein is not detected but the fragments resulting from cleavage thereof (60, 58 and 55 kDa) are detected (FIG. 6C). In contrast, neither whole protein nor cleavage fragments are observed in the heart of WT mice injected with AAV2/9-desm-CAPN3-miR208aT (FIG. 6C), indicative a translational regulation (FIG. 6D). In conclusion, these results show that miR208aT is able to reduce the cardiac toxicity of the CAPN3transgene.

4) Combination of Two Strategies:

New vectors were constructed by combining the promoters CAPN3 and miR-206 and 2 copies of the target sequence of miR-208a: AAV2/9-pC3-CAPN3-miR208aT and AAV2/9-pmiR206-CAPN3-miR208aT. C3KO mice (knockout for calpain 3) received an injection of $1.2 \times 10^{13}$ vg/kg of these vectors.

As previously observed in the wild mice, none of the three vectors (AAV2/9-desm-CAPN3-miR208aT, AAV2/9-pC3-CAPN3-miR208aT and AAV2/9-pmiR206-CAPN3-miR208aT) proved to be toxic for the heart, 3 months after the injection (results not shown).

In contrast, a histological and morphological examination of skeletal muscles of C3KO mice aged 4 weeks and injected with these vectors has shown a positive effect of the expression of calpain 3 on the pathological signs of the murine model. The anterior tibialis (TA) muscles injected with these vectors showed improved histological features compared to those injected with PBS (FIG. 7A). A morphometric analysis of sections of TA muscles stained with HPS revealed a significant decrease in centronuclear fibres (CNF) in the muscles injected with the vector (FIG. 9B left). Similar results were obtained with the PSO muscles (muscle ilio-psoas) although the decrease observed with AAV2/9-pC3-CAPN3-miR208aT and AAV2/9-pmiR206-CAPN3-miR208aT was not statistically significant.

In conclusion, these results indicate that the expression of calpain 3 in skeletal muscles transduced with these recombinant vectors can correct the pathological signs of a mouse deficient in calpain 3, without presenting cardiac toxicity.

BIBLIOGRAPHY

1. Jungbluth H, Wallgren-Pettersson C, Laporte J (2008) Centronuclear (myotubular) myopathy. Orphanet J Rare Dis 3: 26.
2. Wallgren-Pettersson C, Clarke A, Samson F, Fardeau M, Dubowitz V, et al. (1995) The myotubular myopathies: differential diagnosis of the X linked recessive, autosomal dominant, and autosomal recessive forms and present state of DNA studies. J Med Genet 32: 673-679.
3. Herman G, Finegold M, Zhao W, de Gouyon B, Metzenberg A (1999) Medical complications in longterm survivors with X-linked myotubular myopathy. J Pediatr 134: 206-214.
4. Bevilacqua J, Bitoun M, Biancalana V, Oldfors A, Stoltenburg G, et al. (2009) Necklace" fibers, a new histological marker of late-onset MTM1-related centronuclear myopathy. Acta Neuropathol 117: 283-291.
5. Fardeau M (1992) Congenital myopathies. In: Detchant MFLWo, editor. Skeletal muscle pathology. Edinburgh: Churchill Livingstone. pp. 1488-1531.
6. Laporte J, Hu L J, Kretz C, Mandel J L, Kioschis P, et al. (1996) A gene mutated in X-linked myotubular myopathy defines a new putative tyrosine phosphatase family conserved in yeast. Nat Genet 13: 175-182.
7. Dowling J J, Vreede A P, Low S E, Gibbs E M, Kuwada J Y, et al. (2009) Loss of myotubularin function results in T-tubule disorganization in zebrafish and human myotubular myopathy. PLoS Genet 5:e1000372.
8. Buj-Bello A, Laugel V, Messaddeq N, Zahreddine H, Laporte J, et al. (2002) The lipid phosphatase myotubularin is essential for skeletal muscle maintenance but not for myogenesis in mice. Proc Natl Acad Sci USA 99: 15060-15065.

9. Pierson C R, Dulin-Smith A N, Durban A N, Marshall M L, Marshall J T, et al. (2012) Modeling the human MTM1 p.R69C mutation in murine Mtm1 results in exon 4 skipping and a less severe myotubular myopathy phenotype. Hum Mol Genet 21: 811-825.
10. Beggs A H, Bohm J, Snead E, Kozlowski M, Maurer M, et al. (2010) MTM1 mutation associated with X-linked myotubular myopathy in Labrador Retrievers. Proc Natl Acad Sci USA 107: 14697-14702.
11. Al-Qusairi L, Weiss N, Toussaint A, Berbey C, Messaddeq N, et al. (2009) T-tubule disorganization and defective excitation-contraction coupling in muscle fibers lacking myotubularin lipid phosphatase. Proc Natl Acad Sci USA 106: 18763-18768.
12. Hnia K, Tronchere H, Tomczak K K, Amoasii L, Schultz P, et al. (2011) Myotubularin controls desmin intermediate filament architecture and mitochondrial dynamics in human and mouse skeletal muscle. J Clin Invest 121: 70-85.
13. Dowling J J, Joubert R, Low S E, Durban A N, Messaddeq N, et al. (2012) Myotubular myopathy and the neuromuscular junction: a novel therapeutic approach from mouse models. Dis Model Mech.
14. Lawlor M W, Alexander M S, Viola M G, Meng H, Joubert R, et al. (2012) Myotubularin-deficient myoblasts display increased apoptosis, delayed proliferation, and poor cell engraftment. Am J Pathol 181: advanced online.
15. Buj-Bello A, Fougerousse F, Schwab Y, Messaddeq N, Spehner D, et al. (2008) AAV-mediated intramuscular delivery of myotubularin corrects the myotubular myopathy phenotype in targeted murine muscle and suggests a function in plasma membrane homeostasis. Hum Mol Genet 17: 2132-2143.

The invention claimed is:

1. An expression vector for systemic administration comprising:
a nucleic acid sequence encoding a myotubularin polypeptide consisting of the amino acid sequence as set forth in SEQ ID NO: 1, 2, or 3, and at least one additional sequence comprising:
(a) a target sequence of an miRNA expressed in the heart, wherein the target sequence consists of the sequence as set forth in SEQ ID NO: 10, or
(b) a promoter sequence that regulates the expression of the nucleic acid sequence encoding the myotubularin in the heart, and wherein the promoter sequence consists of the nucleic acid sequence as set forth in SEQ ID NO: 12 or SEQ ID NO: 13.

2. The expression vector of claim 1, wherein the myotubularin polypeptide consists of the amino acid sequence as set forth in SEQ ID NO: 1.

3. The expression vector of claim 1, wherein the at least one additional sequence consists of the sequence as set forth in SEQ ID NO: 10.

4. The expression vector of claim 1, wherein the at least one additional sequence consists of the nucleic acid sequence as set forth in SEQ ID NO: 12 or SEQ ID NO: 13.

5. A pharmaceutical composition comprising the expression vector of claim 1.

6. A pharmaceutical composition comprising the expression vector of claim 1, and a pharmaceutically acceptable carrier.

7. The expression vector of claim 3, comprises a desmin promoter, wherein the desmin promoter consists of the nucleic acid sequence as set forth in SEQ ID NO: 11.

8. The expression vector of claim 1, wherein the vector is a viral vector.

9. The expression vector of claim 8, wherein the viral vector is an adeno-associated viral vector (AAV).

10. The expression vector of claim 9, wherein the adeno-associated viral vector is AAV8 or AAV9.

* * * * *

SEQUENCE LISTING

```
<160> NUMBER OF SEQ ID NOS: 29

<210> SEQ ID NO 1
<211> LENGTH: 603
<212> TYPE: PRT
<213> ORGANISM: Homo sapiens
<220> FEATURE:
<223> OTHER INFORMATION: Accession NCBI = NP_000243.1

<400> SEQUENCE: 1

Met Ala Ser Ala Ser Thr Ser Lys Tyr Asn Ser His Ser Leu Glu Asn
1               5                   10                  15

Glu Ser Ile Lys Arg Thr Ser Arg Asp Gly Val Asn Arg Asp Leu Thr
            20                  25                  30

Glu Ala Val Pro Arg Leu Pro Gly Glu Thr Leu Ile Thr Asp Lys Glu
        35                  40                  45

Val Ile Tyr Ile Cys Pro Phe Asn Gly Pro Ile Lys Gly Arg Val Tyr
    50                  55                  60

Ile Thr Asn Tyr Arg Leu Tyr Leu Arg Ser Leu Glu Thr Asp Ser Ser
65                  70                  75                  80

Leu Ile Leu Asp Val Pro Leu Gly Val Ile Ser Arg Ile Glu Lys Met
                85                  90                  95

Gly Gly Ala Thr Ser Arg Gly Glu Asn Ser Tyr Gly Leu Asp Ile Thr
            100                 105                 110

Cys Lys Asp Met Arg Asn Leu Arg Phe Ala Leu Lys Gln Glu Gly His
        115                 120                 125

Ser Arg Arg Asp Met Phe Glu Ile Leu Thr Arg Tyr Ala Phe Pro Leu
    130                 135                 140

Ala His Ser Leu Pro Leu Phe Ala Phe Leu Asn Glu Glu Lys Phe Asn
145                 150                 155                 160

Val Asp Gly Trp Thr Val Tyr Asn Pro Val Glu Glu Tyr Arg Arg Gln
                165                 170                 175

Gly Leu Pro Asn His His Trp Arg Ile Thr Phe Ile Asn Lys Cys Tyr
            180                 185                 190

Glu Leu Cys Asp Thr Tyr Pro Ala Leu Leu Val Val Pro Tyr Arg Ala
        195                 200                 205

Ser Asp Asp Leu Arg Arg Val Ala Thr Phe Arg Ser Arg Asn Arg
    210                 215                 220

Ile Pro Val Leu Ser Trp Ile His Pro Glu Asn Lys Thr Val Ile Val
225                 230                 235                 240
```

```
Arg Cys Ser Gln Pro Leu Val Gly Met Ser Gly Lys Arg Asn Lys Asp
                245                 250                 255

Asp Glu Lys Tyr Leu Asp Val Ile Arg Glu Thr Asn Lys Gln Ile Ser
            260                 265                 270

Lys Leu Thr Ile Tyr Asp Ala Arg Pro Ser Val Asn Ala Val Ala Asn
        275                 280                 285

Lys Ala Thr Gly Gly Gly Tyr Glu Ser Asp Asp Ala Tyr His Asn Ala
    290                 295                 300

Glu Leu Phe Phe Leu Asp Ile His Asn Ile His Val Met Arg Glu Ser
305                 310                 315                 320

Leu Lys Lys Val Lys Asp Ile Val Tyr Pro Asn Val Glu Glu Ser His
                325                 330                 335

Trp Leu Ser Ser Leu Glu Ser Thr His Trp Leu Glu His Ile Lys Leu
            340                 345                 350

Val Leu Thr Gly Ala Ile Gln Val Ala Asp Lys Val Ser Ser Gly Lys
        355                 360                 365

Ser Ser Val Leu Val His Cys Ser Asp Gly Trp Asp Arg Thr Ala Gln
    370                 375                 380

Leu Thr Ser Leu Ala Met Leu Met Leu Asp Ser Phe Tyr Arg Ser Ile
385                 390                 395                 400

Glu Gly Phe Glu Ile Leu Val Gln Lys Glu Trp Ile Ser Phe Gly His
                405                 410                 415

Lys Phe Ala Ser Arg Ile Gly His Gly Asp Lys Asn His Thr Asp Ala
            420                 425                 430

Asp Arg Ser Pro Ile Phe Leu Gln Phe Ile Asp Cys Val Trp Gln Met
        435                 440                 445

Ser Lys Gln Phe Pro Thr Ala Phe Glu Phe Asn Glu Gln Phe Leu Ile
    450                 455                 460

Ile Ile Leu Asp His Leu Tyr Ser Cys Arg Phe Gly Thr Phe Leu Phe
465                 470                 475                 480

Asn Cys Glu Ser Ala Arg Glu Arg Gln Lys Val Thr Glu Arg Thr Val
                485                 490                 495

Ser Leu Trp Ser Leu Ile Asn Ser Asn Lys Glu Lys Phe Lys Asn Pro
            500                 505                 510

Phe Tyr Thr Lys Glu Ile Asn Arg Val Leu Tyr Pro Val Ala Ser Met
        515                 520                 525

Arg His Leu Glu Leu Trp Val Asn Tyr Tyr Ile Arg Trp Asn Pro Arg
    530                 535                 540

Ile Lys Gln Gln Gln Pro Asn Pro Val Glu Gln Arg Tyr Met Glu Leu
545                 550                 555                 560

Leu Ala Leu Arg Asp Glu Tyr Ile Lys Arg Leu Glu Glu Leu Gln Leu
                565                 570                 575

Ala Asn Ser Ala Lys Leu Ser Asp Pro Pro Thr Ser Pro Ser Ser Pro
            580                 585                 590

Ser Gln Met Met Pro His Val Gln Thr His Phe
        595                 600

<210> SEQ ID NO 2
<211> LENGTH: 603
<212> TYPE: PRT
<213> ORGANISM: Mus musculus
<220> FEATURE:
<223> OTHER INFORMATION: Accession NCBI = AAC77821.1

<400> SEQUENCE: 2
```

```
Met Ala Ser Ala Ser Ala Ser Lys Tyr Asn Ser His Ser Leu Glu Asn
 1               5                  10                  15
Glu Ser Ile Lys Lys Val Ser Gln Asp Gly Val Ser Gln Asp Val Ser
            20                  25                  30
Glu Thr Val Pro Arg Leu Pro Gly Glu Leu Leu Ile Thr Glu Lys Glu
        35                  40                  45
Val Ile Tyr Ile Cys Pro Phe Asn Gly Pro Ile Lys Gly Arg Val Tyr
    50                  55                  60
Ile Thr Asn Tyr Arg Leu Tyr Leu Arg Ser Leu Glu Thr Asp Ser Ala
 65                 70                  75                  80
Leu Ile Leu Asp Val Pro Leu Gly Val Ile Ser Arg Ile Glu Tyr Met
                85                  90                  95
Gly Gly Ala Thr Ser Arg Gly Glu Asn Ser Tyr Gly Leu Asp Ile Thr
            100                 105                 110
Cys Lys Asp Leu Arg Asn Leu Arg Phe Ala Leu Lys Gln Glu Gly His
        115                 120                 125
Ser Arg Arg Asp Met Phe Glu Ile Leu Val Lys His Ala Phe Pro Leu
    130                 135                 140
Ala His Asn Leu Pro Leu Phe Ala Phe Val Asn Glu Glu Lys Phe Asn
145                 150                 155                 160
Val Asp Gly Trp Thr Val Tyr Asn Pro Val Glu Glu Tyr Arg Arg Gln
                165                 170                 175
Gly Leu Pro Asn His His Trp Arg Ile Ser Phe Ile Asn Lys Cys Tyr
            180                 185                 190
Glu Leu Cys Glu Thr Tyr Pro Ala Leu Leu Val Val Pro Tyr Arg Thr
        195                 200                 205
Ser Asp Asp Asp Leu Arg Arg Ile Ala Thr Phe Arg Ser Arg Asn Arg
    210                 215                 220
Leu Pro Val Leu Ser Trp Ile His Pro Glu Asn Lys Met Val Ile Met
225                 230                 235                 240
Arg Cys Ser Gln Pro Leu Val Gly Met Ser Gly Lys Arg Asn Lys Asp
                245                 250                 255
Asp Glu Lys Tyr Leu Asp Val Ile Arg Glu Thr Asn Lys Gln Thr Ser
            260                 265                 270
Lys Leu Met Ile Tyr Asp Ala Arg Pro Ser Val Asn Ala Val Ala Asn
        275                 280                 285
Lys Ala Thr Gly Gly Gly Tyr Glu Ser Asp Asp Ala Tyr Gln Asn Ser
    290                 295                 300
Glu Leu Ser Phe Leu Asp Ile His Asn Ile His Val Met Arg Glu Ser
305                 310                 315                 320
Leu Lys Lys Val Lys Asp Ile Val Tyr Pro Asn Ile Glu Glu Ser His
                325                 330                 335
Trp Leu Ser Ser Leu Glu Ser Thr His Trp Leu Glu His Ile Lys Leu
            340                 345                 350
Val Leu Thr Gly Ala Ile Gln Val Ala Asp Gln Val Ser Ser Gly Lys
        355                 360                 365
Ser Ser Val Leu Val His Cys Ser Asp Gly Trp Asp Arg Thr Ala Gln
    370                 375                 380
Leu Thr Ser Leu Ala Met Leu Met Leu Asp Ser Phe Tyr Arg Thr Ile
385                 390                 395                 400
Glu Gly Phe Glu Ile Leu Val Gln Lys Glu Trp Ile Ser Phe Gly His
                405                 410                 415
Lys Phe Ala Ser Arg Ile Gly His Gly Asp Lys Asn His Ala Asp Ala
```

```
                        420                 425                 430
Asp Arg Ser Pro Ile Phe Leu Gln Phe Ile Asp Cys Val Trp Gln Met
                435                 440                 445

Ser Lys Gln Phe Pro Thr Ala Phe Glu Phe Asn Glu Gly Phe Leu Ile
    450                 455                 460

Thr Val Leu Asp His Leu Tyr Ser Cys Arg Phe Gly Thr Phe Leu Phe
465                 470                 475                 480

Asn Cys Asp Ser Ala Arg Glu Arg Gln Lys Leu Thr Glu Arg Thr Val
                485                 490                 495

Ser Leu Trp Ser Leu Ile Asn Ser Asn Lys Asp Lys Phe Lys Asn Pro
            500                 505                 510

Phe Tyr Thr Lys Glu Ile Asn Arg Val Leu Tyr Pro Val Ala Ser Met
        515                 520                 525

Arg His Leu Glu Leu Trp Val Asn Tyr Tyr Ile Arg Trp Asn Pro Arg
    530                 535                 540

Val Lys Gln Gln Gln Pro Asn Pro Val Glu Gln Arg Tyr Met Glu Leu
545                 550                 555                 560

Leu Ala Leu Arg Asp Asp Tyr Ile Lys Arg Leu Glu Glu Leu Gln Leu
                565                 570                 575

Ala Asn Ser Ala Lys Leu Ala Asp Ala Pro Ala Ser Thr Ser Ser Ser
            580                 585                 590

Ser Gln Met Val Pro His Val Gln Thr His Phe
        595                 600

<210> SEQ ID NO 3
<211> LENGTH: 603
<212> TYPE: PRT
<213> ORGANISM: Canis lupus
<220> FEATURE:
<223> OTHER INFORMATION: Accession NCBI = XP_855209.1

<400> SEQUENCE: 3

Met Ala Ser Ala Pro Thr Ser Lys Tyr Asn Ser His Ser Leu Glu Asn
  1               5                  10                  15

Glu Ser Ile Lys Arg Thr Ser Arg Asp Gly Val Asn Trp Asp Leu Ser
                20                  25                  30

Glu Ala Val Pro Arg Leu Pro Gly Glu Thr Arg Ile Thr Asp Lys Glu
            35                  40                  45

Val Ile Tyr Ile Cys Pro Phe Asn Gly Pro Ile Lys Gly Arg Val Tyr
        50                  55                  60

Ile Thr Asn Tyr Arg Leu Tyr Leu Arg Ser Leu Glu Thr Asp Ser Ala
 65                 70                  75                  80

Leu Ile Leu Asp Val Pro Leu Gly Val Ile Ser Arg Ile Glu Lys Met
                85                  90                  95

Gly Gly Ala Thr Ser Arg Gly Glu Asn Ser Tyr Gly Leu Asp Ile Thr
            100                 105                 110

Cys Lys Asp Met Arg Asn Leu Arg Phe Ala Leu Lys Gln Glu Gly His
        115                 120                 125

Ser Arg Arg Asp Met Phe Glu Ile Leu Thr Arg Tyr Ala Phe Pro Leu
    130                 135                 140

Ala His Ser Leu Pro Ile Phe Ala Phe Leu Asn Glu Glu Lys Phe Asn
145                 150                 155                 160

Val Asp Gly Trp Thr Val Tyr Asn Pro Val Glu Glu Tyr Arg Arg Gln
                165                 170                 175

Gly Leu Pro Asn His His Trp Arg Ile Thr Phe Ile Asn Lys Cys Tyr
```

```
            180                 185                 190
Glu Leu Cys Asp Thr Tyr Pro Ala Leu Leu Val Val Pro Tyr Arg Ala
            195                 200                 205

Ser Asp Asp Asp Leu Arg Arg Val Ala Thr Phe Arg Ser Arg Asn Arg
            210                 215                 220

Ile Pro Val Leu Ser Trp Ile His Pro Glu Asn Lys Thr Val Ile Val
225                 230                 235                 240

Arg Cys Ser Gln Pro Leu Val Gly Met Ser Gly Lys Arg Asn Lys Asp
            245                 250                 255

Asp Glu Lys Tyr Leu Asp Val Ile Arg Glu Thr Asn Arg Gln Ile Ser
            260                 265                 270

Lys Leu Thr Ile Tyr Asp Ala Arg Pro Asn Val Asn Ala Val Ala Asn
            275                 280                 285

Lys Ala Thr Gly Gly Gly Tyr Glu Ser Asp Asp Ala Tyr His Asn Ala
            290                 295                 300

Glu Leu Phe Phe Leu Asp Ile His Asn Ile His Val Met Arg Glu Ser
305                 310                 315                 320

Leu Lys Lys Val Lys Asp Ile Val Tyr Pro Asn Val Glu Glu Ser His
            325                 330                 335

Trp Leu Ser Ser Leu Glu Ser Thr His Trp Leu Glu His Ile Lys Leu
            340                 345                 350

Val Leu Thr Gly Ala Ile Gln Val Ala Asp Arg Val Ser Ser Gly Lys
            355                 360                 365

Ser Ser Val Leu Val His Cys Ser Asp Gly Trp Asp Arg Thr Ala Gln
            370                 375                 380

Leu Thr Ser Leu Ala Met Leu Met Leu Asp Ser Phe Tyr Arg Ser Ile
385                 390                 395                 400

Glu Gly Phe Glu Ile Leu Val Gln Lys Glu Trp Ile Ser Phe Gly His
            405                 410                 415

Lys Phe Ala Ser Arg Ile Gly His Gly Asp Lys Asn His Ala Asp Ala
            420                 425                 430

Asp Arg Ser Pro Ile Phe Leu Gln Phe Ile Asp Cys Val Trp Gln Met
            435                 440                 445

Ser Lys Gln Phe Pro Thr Ala Phe Glu Phe Asn Glu Arg Phe Leu Ile
            450                 455                 460

Thr Ile Leu Asp His Leu Tyr Ser Cys Arg Phe Gly Thr Phe Leu Tyr
465                 470                 475                 480

Asn Cys Glu Ser Ala Arg Glu Lys Gln Lys Val Thr Glu Arg Thr Val
            485                 490                 495

Ser Leu Trp Ser Leu Ile Asn Ser Asn Lys Asp Lys Phe Lys Asn Pro
            500                 505                 510

Phe Tyr Thr Lys Glu Ile Asn Arg Val Leu Tyr Pro Val Ala Ser Met
            515                 520                 525

Arg His Leu Glu Leu Trp Val Asn Tyr Tyr Ile Arg Trp Asn Pro Arg
            530                 535                 540

Ile Lys Gln Gln Gln Pro Asn Pro Val Glu Gln Arg Tyr Val Glu Leu
545                 550                 555                 560

Leu Ala Leu Arg Asp Glu Tyr Ile Gln Arg Leu Glu Glu Leu Gln Leu
            565                 570                 575

Ala Ser Ser Ala Lys Leu Pro Asp Pro Ser Thr Ser Pro Ala Gly Pro
            580                 585                 590

Ser Gln Met Met Pro His Val Arg Thr His Phe
            595                 600
```

<210> SEQ ID NO 4
<211> LENGTH: 3452
<212> TYPE: DNA
<213> ORGANISM: Homo sapiens
<220> FEATURE:
<221> NAME/KEY: source
<222> LOCATION: (1)...(3452)
<223> OTHER INFORMATION: mol_type = unassigned DNA
      note = Accession NCBI NM_000252.2
      organism =  Homo sapiens

<400> SEQUENCE: 4

| | | | | | |
|---|---|---|---|---|---|
| agaggggcg | gagcagggcc | cggcagccga | gcagcctggc | aacggcggtg | gcgcccggag | 60 |
| cccgagagtt | tccaggatgg | cttctgcatc | aacttctaaa | tataattcac | actccttgga | 120 |
| gaatgagtct | attaagagga | cgtctcgaga | tggagtcaat | cgagatctca | ctgaggctgt | 180 |
| tcctcgactt | ccaggagaaa | cactaatcac | tgacaaagaa | gttatttaca | tatgtccttt | 240 |
| caatggcccc | attaagggaa | gagtttacat | cacaaattat | cgtctttatt | taagaagttt | 300 |
| ggaaacggat | tcttctctaa | tacttgatgt | tcctctgggt | gtgatctcga | gaattgaaaa | 360 |
| aatgggaggc | gcgacaagta | gaggagaaaa | ttcctatggt | ctagatatta | cttgtaaaga | 420 |
| catgagaaac | ctgaggttcg | ctttgaaaca | ggaaggccac | agcagaagag | atatgtttga | 480 |
| gatcctcacg | agatacgcgt | ttcccctggc | tcacagtctg | ccattatttg | catttttaaa | 540 |
| tgaagaaaag | tttaacgtgg | atggatggac | agtttacaat | ccagtggaag | aatacaggag | 600 |
| gcagggcttg | cccaatcacc | attggagaat | aactttattt | aataagtgct | atgagctctg | 660 |
| tgacacttac | cctgctcttt | tggtggttcc | gtatcgtgcc | tcagatgatg | acctccggag | 720 |
| agttgcaact | tttaggtccc | gaaatcgaat | tccagtgctg | tcatggattc | atccagaaaa | 780 |
| taagacggtc | attgtgcgtt | gcagtcagcc | tcttgtcggt | atgagtggga | aacgaaataa | 840 |
| agatgatgag | aaatatctcg | atgttatcag | ggagactaat | aaacaaattt | ctaaactcac | 900 |
| catttatgat | gcaagaccca | gcgtaaatgc | agtggccaac | aaggcaacag | gaggaggata | 960 |
| tgaaagtgat | gatgcatatc | ataacgccga | acttttcttc | ttagacattc | ataatattca | 1020 |
| tgttatgcgg | gaatctttaa | aaaaagtgaa | ggacattgtt | tatcctaatg | tagaagaatc | 1080 |
| tcattggttg | tccagtttgg | agtctactca | ttggttagaa | catatcaagc | tcgttttgac | 1140 |
| aggagccatt | caagtagcag | acaaagtttc | ttcagggaag | agttcagtgc | ttgtgcattg | 1200 |
| cagtgacgga | tgggacagga | ctgctcagct | gacatccttg | gccatgctga | tgttggatag | 1260 |
| cttctatagg | agcattgaag | ggttcgaaat | actggtacaa | aaagaatgga | taagttttgg | 1320 |
| acataaatt | gcatctcgaa | taggtcatgg | tgataaaaac | cacaccgatg | ctgaccgttc | 1380 |
| tcctattttt | ctccagttta | ttgattgtgt | gtggcaaatg | tcaaaacagt | ccctacagc | 1440 |
| ttttgaattc | aatgaacaat | ttttgattat | aattttggat | catctgtata | gttgccgatt | 1500 |
| tggtactttc | ttattcaact | gtgaatctgc | tcgagaaaga | cagaaggtta | cagaaaggac | 1560 |
| tgtttcttta | tggtcactga | taaacagtaa | taaagaaaaa | ttcaaaaacc | ccttctatac | 1620 |
| taaagaaatc | aatcgagttt | tatatccagt | tgccagtatg | cgtcacttgg | aactctgggt | 1680 |
| gaattactac | attagatgga | accccaggat | caagcaacaa | cagccgaatc | cagtggagca | 1740 |
| gcgttacatg | gagctcttag | ccttacgcga | cgaatacata | aagcggcttg | aggaactgca | 1800 |
| gctcgccaac | tctgccaagc | tttctgatcc | cccaacttca | ccttccagtc | cttcgcaaat | 1860 |
| gatgccccat | gtgcaaactc | acttctgagg | ggggaccctg | gcaccgcatt | agagctcgaa | 1920 |

```
ataaaggcga tagctgactt tcatttgggg catttgtaaa agtagatta aaatatttgc    1980 ctccatgtag aacttgaact aacataatct taaactcttg aatatgtgcc ttctagaata    2040
catattacaa gaaaactaca gggtccacac ggcaatcaga agaaaggagc tgagatgagg    2100
ttttggaaaa ccctgacacc tttaaaaagc agttttttgaa agacaaaatt tagatttaat   2160
ttacgtcttg agaaatacta tatatacaat atatattttg tgggcttaat tgaaacaaca    2220
ttattttaaa atcaaagggg atatatgttt gtggaatgga ttttcctgaa gctgcttaac    2280
agttgctttg gattctctaa gatgaatcca aatgtgaaag atgcatgtta ctgccaaaac    2340
caaattgagc tcagcttcct aggcattacc caaaagcaag gtgtttaagt aattgccagc    2400
ttttatacca tcatgagtgg tgacttaagg agaaatagct gtatagatga gttttcatt     2460 atttggaaat ttaggggtag aaaatgttt cccctaattt tccagagaag cctattttta     2520
tatttttaaa aaactgacag ggcccagtta aatatgattt gcatttttta aatttgccag    2580
ttttattttc taaattcttt catgagcttg cctaaaattc ggaatggttt tcgggttgtg    2640
gcaaacccca aagagagcac tgtccaagga tgtcggagc atcctgctgc ttaggggaat     2700
gttttcgcaa atgttgctct agtcagtcca gctcatctgc caaaatgtag ggctaccgtc    2760
ttggatgcat gagctattgc tagagcatca tccttagaaa tcagtgcccc agatgtacat    2820
gtgttgagcg tattcttgaa agtattgtgt ttatgcattt caatttcaat ggtgttggct    2880
tcccctcccc accccacgcg tgcataaaaa ctggttctac aaattttttac ttgaagtacc   2940 aggccgtttg cttttcagg ttgttttgtt ttatagtatt aagtgaaatt ttaaatgcac     3000
agttctattt gctatctgaa ctaattcatt tattaagtat atttgtaaaa gctaaggctc    3060
gagttaaaac aatgaagtgt tttacaatga tttgtaaagg actatttata actaatatgg    3120
ttttgttttc aatgaattaa gaaagattaa atatatcttt gtaaattatt ttatgtcata    3180
gtttaattgg tctaccaagt aagacatctc aaatacagta gtataatgta tgaattttgt    3240
aagtataaga aattttatta gacattctct tactttttgt aaatgctgta aatatttcat    3300
aaattaacaa agtgtcactc cataaaaaga aagctaatac taatagccta aaagattttg    3360
tgaaatttca tgaaaacttt ttaatggcaa taatgactaa agacctgctg taataaatgt    3420
attaactgaa acctaaaaaa aaaaaaaaaa aa                                  3452
```

<210> SEQ ID NO 5
<211> LENGTH: 3339
<212> TYPE: DNA
<213> ORGANISM: Mus musculus
<220> FEATURE:
<221> NAME/KEY: source
<222> LOCATION: (1)...(3339)
<223> OTHER INFORMATION: mol_type = unassigned DNA
      note = Accession NCBI AF_073996
      organism = Mus musculus

<400> SEQUENCE: 5

```
cggtgagttc gctttcttgg ctgacctggc tcggagccgg gcattgcggg gatccaggat     60
tggaaaggtt ccaggatggc ttctgcatca gcatctaagt ataattcaca ctccttggag    120
aatgaatcca ttaagaaagt gtctcaagat ggagtcagtc aggatgtgag tgagactgtc    180
cctcggctcc caggggagtt actaattact gaaaagaag ttatttacat atgtcctttc     240
aatggcccca ttaagggaag agtttacatc acaaattatc gtctttatttt aagaagtttg   300 gaaacgatt ctgctctaat acttgatgtt cctctgggtg tgatatcaag aattgaatat     360
atgggaggcg cgactagtag aggagaaaat tcctatggtc tagatattac ttgtaaagat    420
```

```
ttgagaaacc tgaggtttgc attgaagcaa aaggccaca gcagaagaga tatgtttgag      480
atccttgtaa aacatgcctt tcctctggca cacaatctgc cattatttgc atttgtaaat      540
gaagagaagt ttaacgtgga tgggtggact gtttataatc cagttgaaga atatagaagg      600
cagggcctgc ccaatcacca ttggaggata agttttatta acaagtgcta tgagctctgt      660
gagacatacc ctgctctttt ggtggttccc tatcggacct cagatgatga tcttaggagg      720
atcgcaacgt ttagatcccg aaatcggctt cctgtactgt cgtggattca cccagaaaac      780
aaaatggtca ttatgcgctg cagtcagcct cttgtcggta tgagtggtaa aagaaataaa      840
gatgacgaga aatacctgga tgtgatcagg gaaactaaca acaaacttc taagctcatg       900 atttatgatg cacgacccag tgtaaatgca gtcgccaaca aggcaacagg aggaggatat      960
gaaagtgatg acgcatatca aaactcagaa cttttccttct tagacattca taatattcat      1020
gttatgcgag aatcttaaa aaaagtgaaa gatattgttt atcccaacat agaagaatct      1080
cattggttgt ccagtttgga gtctactcat tggttagaac atatcaagct tgttctgacc      1140
ggtgccattc aagtggcaga ccaagtgtct tcaggaaaga gctcggtact tgtgcactgc      1200
agtgacggat gggacaggac cgctcagctg acatccttgg ccatgctgat gttggacagc      1260
ttctacagaa ctattgaagg cttttgagata ttggtacaga aagagtggat aagttttggc      1320
cataaatttg catctagaat aggtcatggt gataaaaacc atgctgatgc tgatcgatct      1380 cctattttc ttcagtttat tgactgtgtg tggcagatgt cgaaacagtt ccccacagct       1440
tttgagttca atgaaggctt tttgattacc gttttggatc atctgtatag ctgtcgattt      1500
ggtactttct tattcaactg tgactcggct cgagaaagac agaaacttac agaaagaaca      1560
gtttctctat ggtcgctaat taacagcaat aaagacaaat tcaaaaccc cttctataca       1620 aaagaaatca atcgggtttt gtatccagtt gccagcatgc gtcacttgga actgtgggtg      1680
aattattaca tccgatggaa tcccagggtc aagcagcaac agcccaaccc agtggagcag      1740
cgttacatgg agcttttggc cttgcgtgac gattatataa agaggctcga ggaattgcag      1800
ctggccaact ccgccaagct tgctgatgcc cccgcttcga cttccagttc gtcacagatg      1860
gtgccccatg tgcagacgca cttctgaggg gactcacttc tggcactgca cttgaactct      1920
agataagtga aatagctgac tctcattctg ggcatgtgga caaagtagat ttaaagtgtc      1980
tgcctccatt tagaagttca actaacatct tagacttttg agtatgtgcc ttctgtaata      2040
catatcacaa gaaatcgatg gtgtccgtgt ggcaatcata aggaaggagt caagaggggg      2100
ttctggaaaa tcctcatact ttttttttaca aagcacttt gcaaagataa aacttaaatt       2160
taatttacct ctatataaat tctacatata cagtatgtat tttgtgggct taattgaaat      2220
attattttaa atccaggggg gagatttgtt tgcaaaatgt attttcctcc agctgcttat      2280
aacagttgct ttggattatc taaaattaat ccaaatgtga agatgggta ttactgccaa        2340 agccaaattg cactctgctt cttcagcaaa ttccaagagc aaggcgttta ataattgcc         2400 aattttatt ttaccataag tggtaaggta aaaagaaaga tgaacatttc atcattttga        2460 attttgaaa ataaaaggtt ctcccatcat ttttcaagag aagcacattt ttatattaag         2520
aaaaagtgat aaggtttgat ttttttttcc ctcaacattc tcagctttgc tttctaaatt      2580
atcccatgat ttttgtctaa cactgagtca tactcaggtt gaaggaaacc cataaatagc      2640
actgtgcgag gagctggctg gcttctgctg cttagaggaa tatgttcgca acatgcctc       2700 tagtcaattc gccttatctg ctgaagtgta ggggcaccgc cttgaatgga tgagctatgg      2760
```

| | |
|---|---:|
| ctagagcatc tttctttaca gtaatgcccc aggtgtattc tgtttatgtc tctctgttta | 2820 |
| aatggtgtgc gtgcataaaa acttgctctg cacattatta cttgaagtac tgggcaattt | 2880 |
| gcttttcag gtttttttc attttgtttt gtagtatgaa atggaatttt aaatgcacag | 2940 |
| ttctatttga tatccgaact aattcattta gtaaatatat ttgtaaaagc taaagttaaa | 3000 |
| tcaattaatg ttttacagtg atttgtaaag gattatttat agctaatatg gttttgtttt | 3060 |
| cagtgaatta agagagatta catttatctt tgtaaattat tttatgtcat agcttaatgg | 3120 |
| cctaccaaat gagacatctc aaatataata gtaatgta tggattttgt aagtataaaa | 3180 |
| attattagat attcgtttgc tttttgtaaa cactgtaaat atttcataaa ttaaaatgtg | 3240 |
| tcactccata agaagaaaaa actaatacta atagttgaca ggaattggtg aaatttcatg | 3300 |
| aaaatatttt cattgcaata atattaaaa gacctgctg | 3339 |

<210> SEQ ID NO 6
<211> LENGTH: 1841
<212> TYPE: DNA
<213> ORGANISM: Canis lupus
<220> FEATURE:
<221> NAME/KEY: source
<222> LOCATION: (1)...(1841)
<223> OTHER INFORMATION: mol_type = unassigned DNA
    note = Accession NCBI XM_850116
    organism = Canis lupus

<400> SEQUENCE: 6

| | |
|---|---:|
| cggtggcgcc cggaccccga gtttccagta tggcttctgc accaacttct aaatataatt | 60 |
| cacactcctt ggagaacgag tctattaaga ggacttctag ggatggagtt aattgggacc | 120 |
| tgagtgaggc tgttcctcga cttccaggag aaactcgtat cactgacaaa gaagttattt | 180 |
| acatatgtcc tttcaatggc cccattaagg gaagagttta catcacaaat tatcgtcttt | 240 |
| atttaagaag tttggaaacg gattctgctc taatacttga tgttcctctg ggtgtgatct | 300 |
| ccagaattga aaaatggga ggcgcgacaa gtagaggaga aaattcgtat ggtctagata | 360 |
| ttacttgtaa agacatgagg aacttgaggt tcgcgctgaa acaggaaggc cacagcagga | 420 |
| gggatatgtt tgagatcctc acaagatacg ccttcccctt ggcccacagt ctgccaatat | 480 |
| ttgcatttct aaacgaagaa aagtttaacg tggatgggtg gacagtttat aatccagtcg | 540 |
| aagaatacag aaggcagggc ttgcccaatc accactggag aataactttt atcaacaagt | 600 |
| gctatgagct ctgtgacact tatcctgctc tcttggtggt tccatatcgt gcctcagatg | 660 |
| acgatctcag gagagttgca acttttagat ccagaaatcg aattccagtg ctgtcatgga | 720 |
| ttcatccaga aaacaagacg gtcattgtgc gctgcagcca gcctcttgtc ggaatgagtg | 780 |
| gtaaacggaa taaagatgat gagaagtatc tcgatgttat cagggagact aacagacaaa | 840 |
| tttctaaact cacaatctat gatgccagac ccaatgtaaa tgccgtggcc aacaaggcaa | 900 |
| caggaggagg atatgaaagt gatgatgcat atcataacgc cgaactttc ttcttagaca | 960 |
| ttcataacat tcatgttatg cgggaatctt taaaaaagt caaagacatc gtttatccta | 1020 |
| atgtggaaga gtctcactgg ctgtccagtt tggagtctac ccattggtta gaacatatca | 1080 |
| agcttgtttt gacgggagcc attcaagtag cagacagagt ttcttcaggg aagagctcag | 1140 |
| tgctcgtgca ctgcagcgat ggatgggaca ggactgccca gctgacgtcc ttggccatgc | 1200 |
| tgatgctcga cagcttctat cggagcatcg agggctttga aatattggta caaaaggaat | 1260 |
| ggataagttt tggacataag tttgcatcta gaataggtca tggtgataaa aaccacgccg | 1320 |
| acgctgaccg gtctcctatt tttctccagt ttattgattg tgtatggcaa atgtcaaaac | 1380 |

```
agttccctac agcttttgaa ttcaatgaac gattttttgat tacaattttg gatcatctgt    1440
atagttgccg gtttggtacc ttcttgtaca actgtgaatc tgctcgggaa aaacagaaag    1500
tgacggaacg aacagtatct ttatggtcac tgataaacag taataaggac aaattcaaaa    1560
atcccttcta tactaaagaa atcaatcgag ttttatatcc agttgccagt atgcgtcact    1620
tggaactttg ggtgaattac tacattagat ggaaccccag gatcaagcaa caacagccca    1680
acccagtgga gcagcggtac gtggagctgt tggccttgcg tgacgaatac atacagcggc    1740
tcgaggagct gcagctcgcc agctcggcca agctgcccga ccctcgacc tcaccggccg    1800 ggccctcgca gatgatgccg cacgtgcgca cacacttctg a                         1841
```

<210> SEQ ID NO 7
<211> LENGTH: 821
<212> TYPE: PRT
<213> ORGANISM: Homo sapiens
<220> FEATURE:
<223> OTHER INFORMATION: Accession NCBI = NP_000061.1

<400> SEQUENCE: 7

```
Met Pro Thr Val Ile Ser Ala Ser Val Ala Pro Arg Thr Ala Ala Glu
 1               5                  10                  15

Pro Arg Ser Pro Gly Pro Val Pro His Pro Ala Gln Ser Lys Ala Thr
             20                  25                  30

Glu Ala Gly Gly Gly Asn Pro Ser Gly Ile Tyr Ser Ala Ile Ile Ser
         35                  40                  45

Arg Asn Phe Pro Ile Ile Gly Val Lys Glu Lys Thr Phe Glu Gln Leu
     50                  55                  60

His Lys Lys Cys Leu Glu Lys Lys Val Leu Tyr Val Asp Pro Glu Phe
 65                  70                  75                  80

Pro Pro Asp Glu Thr Ser Leu Phe Tyr Ser Gln Lys Phe Pro Ile Gln
                 85                  90                  95

Phe Val Trp Lys Arg Pro Pro Glu Ile Cys Glu Asn Pro Arg Phe Ile
            100                 105                 110

Ile Asp Gly Ala Asn Arg Thr Asp Ile Cys Gln Gly Glu Leu Gly Asp
        115                 120                 125

Cys Trp Phe Leu Ala Ala Ile Ala Cys Leu Thr Leu Asn Gln His Leu
    130                 135                 140

Leu Phe Arg Val Ile Pro His Asp Gln Ser Phe Ile Glu Asn Tyr Ala
145                 150                 155                 160

Gly Ile Phe His Phe Gln Phe Trp Arg Tyr Gly Glu Trp Val Asp Val
                165                 170                 175

Val Ile Asp Asp Cys Leu Pro Thr Tyr Asn Asn Gln Leu Val Phe Thr
            180                 185                 190

Lys Ser Asn His Arg Asn Glu Phe Trp Ser Ala Leu Leu Glu Lys Ala
        195                 200                 205

Tyr Ala Lys Leu His Gly Ser Tyr Glu Ala Leu Lys Gly Gly Asn Thr
    210                 215                 220

Thr Glu Ala Met Glu Asp Phe Thr Gly Gly Val Ala Glu Phe Phe Glu
225                 230                 235                 240

Ile Arg Asp Ala Pro Ser Asp Met Tyr Lys Ile Met Lys Lys Ala Ile
                245                 250                 255

Glu Arg Gly Ser Leu Met Gly Cys Ser Ile Asp Asp Gly Thr Asn Met
            260                 265                 270

Thr Tyr Gly Thr Ser Pro Ser Gly Leu Asn Met Gly Glu Leu Ile Ala
```

```
                275                 280                 285
Arg Met Val Arg Asn Met Asp Asn Ser Leu Leu Gln Asp Ser Asp Leu
290                 295                 300

Asp Pro Arg Gly Ser Asp Glu Arg Pro Thr Arg Thr Ile Ile Pro Val
305                 310                 315                 320

Gln Tyr Glu Thr Arg Met Ala Cys Gly Leu Val Arg Gly His Ala Tyr
                325                 330                 335

Ser Val Thr Gly Leu Asp Glu Val Pro Phe Lys Gly Glu Lys Val Lys
                340                 345                 350

Leu Val Arg Leu Arg Asn Pro Trp Gly Gln Val Glu Trp Asn Gly Ser
                355                 360                 365

Trp Ser Asp Arg Trp Lys Asp Trp Ser Phe Val Asp Lys Asp Glu Lys
370                 375                 380

Ala Arg Leu Gln His Gln Val Thr Glu Asp Gly Glu Phe Trp Met Ser
385                 390                 395                 400

Tyr Glu Asp Phe Ile Tyr His Phe Thr Lys Leu Glu Ile Cys Asn Leu
                405                 410                 415

Thr Ala Asp Ala Leu Gln Ser Asp Lys Leu Gln Thr Trp Thr Val Ser
                420                 425                 430

Val Asn Glu Gly Arg Trp Val Arg Gly Cys Ser Ala Gly Gly Cys Arg
                435                 440                 445

Asn Phe Pro Asp Thr Phe Trp Thr Asn Pro Gln Tyr Arg Leu Lys Leu
450                 455                 460

Leu Glu Glu Asp Asp Pro Asp Asp Ser Glu Val Ile Cys Ser Phe
465                 470                 475                 480

Leu Val Ala Leu Met Gln Lys Asn Arg Arg Lys Asp Arg Lys Leu Gly
                485                 490                 495

Ala Ser Leu Phe Thr Ile Gly Phe Ala Ile Tyr Glu Val Pro Lys Glu
                500                 505                 510

Met His Gly Asn Lys Gln His Leu Gln Lys Asp Phe Phe Leu Tyr Asn
                515                 520                 525

Ala Ser Lys Ala Arg Ser Lys Thr Tyr Ile Asn Met Arg Glu Val Ser
530                 535                 540

Gln Arg Phe Arg Leu Pro Pro Ser Glu Tyr Val Ile Val Pro Ser Thr
545                 550                 555                 560

Tyr Glu Pro His Gln Glu Gly Glu Phe Ile Leu Arg Val Phe Ser Glu
                565                 570                 575

Lys Arg Asn Leu Ser Glu Glu Val Glu Asn Thr Ile Ser Val Asp Arg
                580                 585                 590

Pro Val Lys Lys Lys Thr Lys Pro Ile Ile Phe Val Ser Asp Arg
                595                 600                 605

Ala Asn Ser Asn Lys Glu Leu Gly Val Asp Gln Glu Ser Glu Glu Gly
610                 615                 620

Lys Gly Lys Thr Ser Pro Asp Lys Gln Lys Ser Pro Gln Pro Gln
625                 630                 635                 640

Pro Gly Ser Ser Asp Gln Glu Ser Glu Glu Gln Gln Phe Arg Asn
                645                 650                 655

Ile Phe Lys Gln Ile Ala Gly Asp Asp Met Glu Ile Cys Ala Asp Glu
                660                 665                 670

Leu Lys Lys Val Leu Asn Thr Val Val Asn Lys His Lys Asp Leu Lys
                675                 680                 685

Thr His Gly Phe Thr Leu Glu Ser Cys Arg Ser Met Ile Ala Leu Met
                690                 695                 700
```

Asp Thr Asp Gly Ser Gly Lys Leu Asn Leu Gln Glu Phe His His Leu
705                 710                 715                 720

Trp Asn Lys Ile Lys Ala Trp Gln Lys Ile Phe Lys His Tyr Asp Thr
            725                 730                 735

Asp Gln Ser Gly Thr Ile Asn Ser Tyr Glu Met Arg Asn Ala Val Asn
            740                 745                 750

Asp Ala Gly Phe His Leu Asn Asn Gln Leu Tyr Asp Ile Ile Thr Met
            755                 760                 765

Arg Tyr Ala Asp Lys His Met Asn Ile Asp Phe Asp Ser Phe Ile Cys
            770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
            820

<210> SEQ ID NO 8
<211> LENGTH: 3316
<212> TYPE: DNA
<213> ORGANISM: Homo sapiens
<220> FEATURE:
<221> NAME/KEY: source
<222> LOCATION: (1)...(3316)
<223> OTHER INFORMATION: mol_type = unassigned DNA
      note = Accession NCBI NM_000070
      organims = Homo sapiens

<400> SEQUENCE: 8

```
cactctcttt ctctctccct ctggcatgca tgctgctggt aggagacccc caagtcaaca      60
ttgcttcaga atcctttag cactcatttc tcaggagaac ttatggcttc agaatcacag     120
ctcggttttt aagatggaca taacctgtac gaccttctga tgggctttca actttgaact    180
ggatgtggac acttttctct cagatgacag aattactcca acttcccctt tgcagttgct    240
tcctttcctt gaaggtagct gtatcttatt ttctttaaaa agcttttct tccaaagcca    300
cttgccatgc cgaccgtcat tagcgcatct gtggctccaa ggacagcggc tgagccccgg    360
tccccagggc cagttcctca cccggcccag agcaaggcca ctgaggctgg gggtggaaac    420
ccaagtggca tctattcagc catcatcagc cgcaattttc ctattatcgg agtgaaagag    480
aagacattcg agcaacttca caagaaatgt ctagaaaaga agttcttta tgtggaccct    540
gagttcccac cggatgagac ctctctcttt tatagccaga agttccccat ccagttcgtc    600
tggaagagac ctccggaaat tgcgagaat ccccgattta tcattgatgg agccaacaga    660
actgacatct gtcaaggaga gctaggggac tgctggtttc tcgcagccat gcctgcctg    720
accctgaacc agcaccttct tttccgagtc ataccccatg atcaaagttt catcgaaaac    780
tacgcaggga tcttccactt ccagttctgg cgctatggag agtgggtgga cgtggttata    840
gatgactgcc tgccaacgta caacaatcaa ctggttttca ccaagtccaa ccaccgcaat    900
gagttctgga gtgctctgct ggagaaggct tatgctaagc tccatggttc ctacgaagct    960
ctgaaaggtg gaacaccac agaggccatg gaggacttca caggagggt ggcagagttt   1020
tttgagatca gggatgctcc tagtgacatg tacaagatca tgaagaaagc catcgagaga   1080
ggctccctca tgggctgctc cattgatgat gcacgaaca tgacctatgg aacctctcct   1140
tctggtctga acatggggga gttgattgca cggatggtaa ggaatatgga taactcactg   1200
```

-continued

```
ctccaggact cagacctcga ccccagaggc tcagatgaaa gaccgacccg gacaatcatt    1260
ccggttcagt atgagacaag aatggcctgc gggctggtca gaggtcacgc ctactctgtc    1320
acggggctgg atgaggtccc gttcaaaggt gagaaagtga agctggtgcg gctgcggaat    1380
ccgtggggcc aggtggagtg gaacggttct tggagtgata gatggaagga ctggagcttt    1440
gtggacaaag atgagaaggc ccgtctgcag caccaggtca ctgaggatgg agagttctgg    1500
atgtcctatg aggatttcat ctaccatttc acaaagttgg agatctgcaa cctcacggcc    1560
gatgctctgc agtctgacaa gcttcagacc tggacagtgt ctgtgaacga gggccgctgg    1620
gtacggggtt gctctgccgg aggctgccgc aacttcccag atactttctg gaccaaccct    1680
cagtaccgtc tgaagctcct ggaggaggac gatgaccctg atgactcgga ggtgatttgc    1740
agcttcctgg tggccctgat gcagaagaac cggcggaagg accggaagct aggggccagt    1800
ctcttcacca ttggcttcgc catctacgag gttcccaaag agatgcacgg gaacaagcag    1860
cacctgcaga aggacttctt cctgtacaac gcctccaagg ccaggagcaa acctacatc     1920 aacatgcggg aggtgtccca gcgcttccgc ctgcctccca gcgagtacgt catcgtgccc    1980
tccacctacg agccccacca ggaggggaa ttcatcctcc gggtcttctc tgaaaagagg     2040
aacctctctg aggaagttga aaataccatc tccgtggatc ggccagtgaa aagaaaaaa     2100 accaagccca tcatcttcgt ttcggacaga gcaaacagca caaggagct gggtgtggac     2160 caggagtcag aggagggcaa aggcaaaaca agccctgata gcaaaagca gtccccacag     2220 ccacagcctg gcagctctga tcaggaaagt gaggaacagc aacaattccg gaacattttc    2280
aagcagatag caggagatga catggagatc tgtgcagatg agctcaagaa ggtccttaac    2340
acagtcgtga caaacacaa ggacctgaag acacacgggt tcacactgga gtcctgccgt     2400
agcatgattg cgctcatgga tacagatggc tctggaaagc tcaacctgca ggagttccac    2460
cacctctgga caagattaa ggcctggcag aaaattttca acactatga cacagaccag     2520 tccggcacca tcaacagcta cgagatgcga aatgcagtca acgacgcagg attccacctc    2580
aacaaccagc tctatgacat cattaccatg cggtacgcag acaaacacat gaacatcgac    2640
tttgacagtt tcatctgctg cttcgttagg ctggagggca tgttcagagc ttttcatgca    2700
tttgacaagg atggagatgg tatcatcaag ctcaacgttc tggagtggct gcagctcacc    2760
atgtatgcct gaaccaggct ggcctcatcc aaagccatgc aggatcactc aggatttcag    2820 tttcacccctc tatttccaaa gccatttacc tcaaaggacc cagcagctac acccctacag    2880
gcttccaggc acctcatcag tcatgctcct cctccatttt accccctacc catccttgat    2940
cggtcatgcc tagcctgacc ctttagtaaa gcaatgaggt aggaagaaca aacccttgtc    3000
cctttgccat gtggaggaaa gtgcctgcct ctggtccgag ccgcctcggt tctgaagcga    3060
gtgctcctgc ttaccttgct ctaggctgtc tgcagaagca cctgccggtg gcactcagca    3120
cctccttgtg ctagagccct ccatcaccctt cacgctgtcc caccatgggc caggaaccaa    3180
accagcactg ggttctactg ctgtgggta aactaactca gtggaatagg gctggttact     3240
ttgggctgtc caactcataa gtttggctgc attttgaaaa aagctgatct aaataaaggc    3300
atgtgtatgg ctggtc                                                    3316
```

<210> SEQ ID NO 9
<211> LENGTH: 22
<212> TYPE: RNA
<213> ORGANISM: Homo sapiens
<220> FEATURE:
<221> NAME/KEY: source
<222> LOCATION: (1)...(22)
<223> OTHER INFORMATION: mol_type = other RNA
      note = Accession MIMT0000241
      organism = Homo sapiens

<400> SEQUENCE: 9
auaagacgag caaaaagcuu gu                                              22

<210> SEQ ID NO 10
<211> LENGTH: 22
<212> TYPE: DNA
<213> ORGANISM: Homo sapiens
<220> FEATURE:
<221> NAME/KEY: source
<222> LOCATION: (1)...(22)
<223> OTHER INFORMATION: mol_type = unassigned DNA
      organism = Homo sapiens

<400> SEQUENCE: 10
acaagctttt tgctcgtctt at                                              22

<210> SEQ ID NO 11
<211> LENGTH: 1050
<212> TYPE: DNA
<213> ORGANISM: Homo sapiens
<220> FEATURE:
<221> NAME/KEY: source
<222> LOCATION: (1)...(1050)
<223> OTHER INFORMATION: mol_type = unassigned DNA
      note = Promoteur Desmine
      organism  = Homo sapiens

<400> SEQUENCE: 11
cccccacagc tcctctcctg tgccttgttt cccagccatg cgttctcctc tataaatacc       60
cgctctggta tttggggttg gcagctgttg ctgccaggga gatggttggg ttgacatgcg      120
gctcctgaca aaacacaaac ccctggtgtg tgtgggcgtg ggtggtgtga gtaggggat       180 gaatcaggga gggggcgggg gacccagggg gcaggagcca cacaaagtct gtgcgggggt      240
gggagcgcac atagcaattg gaaactgaaa gcttatcaga ccctttctgg aaatcagccc      300 actgttttata aacttgaggc cccaccctcg acagtaccgg ggaggaagag ggcctgcact     360
agtccagagg gaaactgagg ctcagggcca gctcgcccat agacatacat ggcaggcagg      420
ctttggccag gatccctccg cctgccaggc gtctccctgc cctcccttcc tgcctagaga      480
cccccaccct caagcctggc tggtctttgc ctgagaccca aacctcttcg acttcaagag      540
aatatttagg aacaaggtgg tttagggcct ttcctgggaa caggccttga ccctttaaga     600
aatgacccaa agtctctcct tgaccaaaaa ggggaccctc aaactaaagg gaagcctctc      660
ttctgctgtc tccctgacc ccactcccc ccacccagg acgaggagat aaccagggct       720
gaaagaggcc cgcctggggg ctgcagacat gcttgctgcc tgccctggcg aaggattggt      780
aggcttgccc gtcacaggac ccccgctggc tgactcaggg gcgcaggcct cttgcggggg     840
agctggcctc cccgccccca cggccacggg ccgcccttc ctggcaggac agcgggatct      900
tgcagctgtc aggggagggg aggcgggggc tgatgtcagg aggatacaa atagtgccga      960 cggctggggg ccctgtctcc cctcgccgca tccactctcc ggccggccgc ctgcccgccg     1020
cctcctccgt gcgcccgcca gcctcgcccg                                    1050

<210> SEQ ID NO 12
<211> LENGTH: 1654
<212> TYPE: DNA
<213> ORGANISM: Homo sapiens

```
<220> FEATURE:
<221> NAME/KEY: source
<222> LOCATION: (1)...(1654)
<223> OTHER INFORMATION: mol_type = unassigned DNA
      note = Promoteur calpaine 3
      organism  = Homo sapiens

<400> SEQUENCE: 12
cacatgcctc cactctgcca tacttgaaat gtgctcatct ccttacagcc cagggagcag      60
ctattgtggg tagaagacaa ggtggaggcc aggcaggcac ttcccttccc cagagccact     120
tatgctctca tctaagagcc ctgaaaccag gtgtgacatc ccaggagttg acagacagtc     180
tggttcagta tctaattcca acttctgtct cagatgccta atgtggcatg gctgaatgag     240
tcaacatata acctgtacag taagtcctca cttaacatca ttgataggtg cttgtaaact     300
gtgactttaa cgaaaacata ccgtgtgctg tagggactta actcttgttt atatcagtta     360
gcctggtttc actatacagt acatcatttt gcttaaagtc acagcttacg agaacctatc     420
gatgatgtta agtgaggatt ttctctgctc aggtgcactt ttttttttt tttaagacgg      480 agtctctttc tgtcacctgg gctggagtgc agtggcgcga tctgggttca ctacaacctc     540
tgcctcctgg gttcaagcaa ttcttctgtc tcagcctccc aagtagctgg gattacaggc     600
acccgccgcc acaccggct tatttttgta tttttagtag agacagggtt tcactattgt      660
tggccatgct ggtctcgaac tcctgacctc atgtgatcca cccgcctcgg cctcccaaag     720
tgcagagatt agagacgtga gccacatggc ccagcaggac cacttttag cagattcagt      780 cccagtgttc atttttgtgga tggggagaga caagaggtgg caaggtcaag tgtgcaggta     840
gagacaggga ttttctcaaa tgaggactct gctgagtagc attttccatg cagacatttc     900
caatgagcgc tgacccaaga acattctaaa aaagatacca aatctaacat tgaataatgt     960
tctgatatcc taaaatttta ggactaaaaa tcatgttctc taaaattcac agaatatttt    1020
tgtagaattc agtacctccc gttcacccta actagctttt ttgcaatatt gtttttccatt   1080 catttgatgg ccagtagttg ggtggtctgt ataactgcct actcaataac atgtcagcag    1140
ttctcagctt ctttccagtg ttcaccttac tcagatactc cctttttcatt ttctggcaac   1200 accagcactt catggcaaca gaaatgtccc tagccaggtt ctctctctac catgcagtct    1260
ctcttgctct catactcaca gtgtttcttc acatctatttt ttagttttcc tggctcaagc    1320
atcttcaggc cactgaaaca caaccctcac tctctttctc tctccctctg gcatgcatgc    1380
tgctggtagg agaccccaa gtcaacattg cttcagaaat cctttagcac tcatttctca     1440
ggagaactta tggcttcaga atcacagctc ggtttttaag atggacataa cctgtacgac    1500
cttctgatgg gctttcaact ttgaactgga tgtggacact tttctctcag atgacagaat    1560
tactccaact tccccttgtgc agttgcttcc tttccttgaa ggtagctgta tcttattttc   1620
tttaaaaagc tttttcttcc aaagccactt gcca                                1654

<210> SEQ ID NO 13
<211> LENGTH: 805
<212> TYPE: DNA
<213> ORGANISM: Homo sapiens
<220> FEATURE:
<221> NAME/KEY: source
<222> LOCATION: (1)...(805)
<223> OTHER INFORMATION: mol_type = unassigned DNA
      note = promoteur miARN206
      organism = Homo sapiens

<400> SEQUENCE: 13
```

```
gggggccaac tcttcctttg gcatatgttt ccccattttc tggcagagaa tcagatacca      60
caaagttcaa aacccatct ccctccagcc agggtggcca tccagaccct gagtggctca      120
acagctgcca atgtccctca tccttctgag gctcaggcct cacagattgt ggggcaggtg      180
atgggctagg gggagcagaa gcccgacaaa aggatccttc ccacagtgaa caatggtgct      240
tggaatgctg gatgggcagc tgctgcccat caacaagcac ccaaaacaga tagacgtaca      300
gtaggaagta caggagggcc ggtgtgtttc taagcatgag tggctctctg cgtgaatgtg      360
gaaaatttct ctgttggatt ctctcttctt tttaattttc ccttcactgg atcccaaaca      420
ttaaaaaaga atcacattca aaatgcacaa aaacagcagc agtgaattaa ttagtagtaa      480
taacaaagga ctggatagac tgtagctgca caagaataag ccagggaaac gtggtgctgc      540
ttatctgtga acaaacagta ggaaggattt ggtcccaagc agcactgcca ttcctcacaa      600
cagatttatt tcagcatgat ttggtcgggc gggggggatt taggatgagt tgagatccca      660
gtgatcttct cgctaagagt ttcctgcctg ggcaaggagg aaagatgcta caagtggccc      720
acttctgaga tgcgggctgc ttctggatga cactgcttcc cgaggccaca tgcttcttta      780
tatccccata tggattactt tgcta                                          805
```

```
<210> SEQ ID NO 14
<211> LENGTH: 1812
<212> TYPE: DNA
<213> ORGANISM: Mus musculus
<220> FEATURE:
<221> NAME/KEY: source
<222> LOCATION: (1)...(1812)
<223> OTHER INFORMATION: mol_type = unassigned DNA
      note = ORF MTM1
      organism = Mus musculus

<400> SEQUENCE: 14
atggcttctg catcagcatc taagtataat tcacactcct tggagaatga atccattaag      60
aaagtgtctc aagatggagt cagtcaggat gtgagtgaga ctgtccctcg gctcccaggg     120
gagttactaa ttactgaaaa agaagttatt tacatatgtc ctttcaatgg ccccattaag     180
ggaagagttt acatcacaaa ttatcgtctt tatttaagaa gtttggaaac ggattctgct     240
ctaatacttg atgttcctct gggtgtgata tcaagaattg aaaaaatggg aggcgcgaca     300
agtagaggag aaaattccta tggtctagat attacttgta aagatttgag aaacctgagg     360
tttgcattga agcaagaagg ccacagcaga agagatatgt ttgagatcct tgtaaaacat     420
gcctttcctc tggcacacaa tctgccatta tttgcatttg taaatgaaga gaagtttaac     480
gtggatgggt ggactgttta taatccagtt gaagaatata aaggcagggg cctgcccaat     540
caccattgga ggataagttt tattaacaag tgctatgagc tctgtgagac ataccctgct     600
cttttggtgg ttccctatcg gacctcagat gatgatctta ggaggatcgc aacgtttaga     660
tcccgaaatc ggcttcctgt actgtcgtgg attcacccag aaaacaaaat ggtcattatg     720
cgctgcagtc agcctcttgt cggtatgagt ggtaaaagaa ataaagatga cgagaaatac     780
ctggatgtga tcagggaaac taacaaacaa acttctaagc tcatgattta tgatgcacga     840
cccagtgtaa atgcagtcgc caacaaggca acaggaggag gatatgaaag tgatgacgca     900
tatcaaaact cagaactttc cttcttagac attcataata ttcatgttat gcgagaatct      960
ttaaaaaaag tgaaagatat tgtttatccc aacatagaag aatctcattg gttgtccagt     1020
ttggagtcta ctcattggtt agaacatatc aagcttgttc tgaccggtgc cattcaagtg     1080
gcagaccaag tgtcttcagg aaagagctcg gtacttgtgc actgcagtga cggatgggac     1140
```

```
aggaccgctc agctgacatc cttggccatg ctgatgttgg acagcttcta cagaactatt    1200
gaaggctttg atatattggt acagaaagag tggataagtt ttggccataa atttgcatct    1260
agaataggtc atggtgataa aaaccatgct gatgctgatc gatctcctat ttttcttcag    1320
tttattgact gtgtgtggca gatgtcgaaa cagttcccca cagcttttga gttcaatgaa    1380 ggcttttga ttaccgtttt ggatcatctg tatagctgtc gatttggtac tttcttattc     1440
aactgtgact cggctcgaga aagacagaaa cttacagaaa gaacagtttc tctatggtcg    1500
ctaattaaca gcaataaaga caaattcaaa acccccttct atacaaaaga aatcaatcgg    1560
gttttgtatc cagttgccag catgcgtcac ttggaactgt gggtgaatta ttacatccga    1620
tggaatccca gggtcaagca gcaacagccc aacccagtgg agcagcgtta catggagctt    1680
ttggccttgc gtgacgatta tataaagagg ctcgaggaat gcagctggc caactccgcc     1740 aagcttgctg atgccccgc ttcgacttcc agttcgtcac agatggtgcc ccatgtgcag     1800
acgcacttct ga                                                        1812

<210> SEQ ID NO 15
<211> LENGTH: 22
<212> TYPE: DNA
<213> ORGANISM: Artificial Sequence
<220> FEATURE:
<223> OTHER INFORMATION: AAV forward primer

<400> SEQUENCE: 15
ctccatcact aggggttcct tg                                              22

<210> SEQ ID NO 16
<211> LENGTH: 18
<212> TYPE: DNA
<213> ORGANISM: Artificial Sequence
<220> FEATURE:
<223> OTHER INFORMATION: AAV reverse  primer

<400> SEQUENCE: 16
gtagataagt agcatggc                                                   18

<210> SEQ ID NO 17
<211> LENGTH: 17
<212> TYPE: DNA
<213> ORGANISM: Artificial Sequence
<220> FEATURE:
<223> OTHER INFORMATION: AAV probe

<400> SEQUENCE: 17
tagttaatga ttaaccc                                                    17

<210> SEQ ID NO 18
<211> LENGTH: 21
<212> TYPE: DNA
<213> ORGANISM: Artificial Sequence
<220> FEATURE:
<223> OTHER INFORMATION: Titine forward primer

<400> SEQUENCE: 18
aaaacgagca gtgacgtgag c                                               21

<210> SEQ ID NO 19
<211> LENGTH: 20
<212> TYPE: DNA
<213> ORGANISM: Artificial Sequence
<220> FEATURE:
```

-continued

<223> OTHER INFORMATION: Titine reverse primer

<400> SEQUENCE: 19
ttcagtcatg ctgctagcgc                                                20

<210> SEQ ID NO 20
<211> LENGTH: 25
<212> TYPE: DNA
<213> ORGANISM: Artificial Sequence
<220> FEATURE:
<223> OTHER INFORMATION: Titine probe

<400> SEQUENCE: 20
tgcacggaag cgtctcgtct cagtc                                          25

<210> SEQ ID NO 21
<211> LENGTH: 16
<212> TYPE: DNA
<213> ORGANISM: Artificial Sequence
<220> FEATURE:
<223> OTHER INFORMATION: CAPN3sfr.f  primer

<400> SEQUENCE: 21
cgcctccaag gcccgt                                                    16

<210> SEQ ID NO 22
<211> LENGTH: 16
<212> TYPE: DNA
<213> ORGANISM: Artificial Sequence
<220> FEATURE:
<223> OTHER INFORMATION: CAPN3sfr.r primer

<400> SEQUENCE: 22
ggcggaagcg ctggct                                                    16

<210> SEQ ID NO 23
<211> LENGTH: 21
<212> TYPE: DNA
<213> ORGANISM: Artificial Sequence
<220> FEATURE:
<223> OTHER INFORMATION: "MGBTUCAPN3.p probe

<400> SEQUENCE: 23
ctacatcaac atgagagagg t                                              21

<210> SEQ ID NO 24
<211> LENGTH: 16
<212> TYPE: DNA
<213> ORGANISM: Artificial Sequence
<220> FEATURE:
<223> OTHER INFORMATION: CAPN3.f  primer

<400> SEQUENCE: 24
cgcctccaag gccagg                                                    16

<210> SEQ ID NO 25
<211> LENGTH: 16
<212> TYPE: DNA
<213> ORGANISM: Artificial Sequence
<220> FEATURE:
<223> OTHER INFORMATION: CAPN3.r primer

<400> SEQUENCE: 25
ggcggaagcg ctggga                                                    16

```
<210> SEQ ID NO 26
<211> LENGTH: 20
<212> TYPE: DNA
<213> ORGANISM: Artificial Sequence
<220> FEATURE:
<223> OTHER INFORMATION: CAPN3.p probe

<400> SEQUENCE: 26
tacatcaaca tgcgggaggt                                               20

<210> SEQ ID NO 27
<211> LENGTH: 20
<212> TYPE: DNA
<213> ORGANISM: Artificial Sequence
<220> FEATURE:
<223> OTHER INFORMATION: MH181PO.F primer

<400> SEQUENCE: 27
ctccaagcag atgcagcaga                                               20

<210> SEQ ID NO 28
<211> LENGTH: 20
<212> TYPE: DNA
<213> ORGANISM: Artificial Sequence
<220> FEATURE:
<223> OTHER INFORMATION: M267PO.R primer

<400> SEQUENCE: 28
accatgatgc gcaaggctat                                               20

<210> SEQ ID NO 29
<211> LENGTH: 22
<212> TYPE: DNA
<213> ORGANISM: Artificial Sequence
<220> FEATURE:
<223> OTHER INFORMATION: M225PO.p probe

<400> SEQUENCE: 29
ccgtggtgct gatgggcaag aa                                            22
```